United States Patent
Fu et al.

(10) Patent No.: US 10,534,156 B2
(45) Date of Patent: Jan. 14, 2020

(54) DEVICES AND METHODS FOR LENS ALIGNMENT BASED ON ENCODED COLOR PATTERNS

(71) Applicant: FACEBOOK TECHNOLOGIES, LLC, Menlo Park, CA (US)

(72) Inventors: Yijing Fu, Redmond, WA (US); Brian Wheelwright, Sammamish, WA (US); Jacques Gollier, Bellevue, WA (US); Ying Geng, Bellevue, WA (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 15/999,329

(22) Filed: Aug. 17, 2018

(65) Prior Publication Data
US 2019/0018216 A1    Jan. 17, 2019

Related U.S. Application Data

(63) Continuation-in-part of application No. 15/583,952, filed on May 1, 2017, now Pat. No. 10,254,507.

(51) Int. Cl.
*A61B 3/10*        (2006.01)
*G02B 7/12*        (2006.01)
(Continued)

(52) U.S. Cl.
CPC ............... *G02B 7/12* (2013.01); *A61B 3/111* (2013.01); *G02B 27/0172* (2013.01); *G02B 27/0179* (2013.01); *G02B 2027/0112* (2013.01); *G02B 2027/0123* (2013.01); *G02B 2027/0161* (2013.01); *G02B 2027/0187* (2013.01)

(58) Field of Classification Search
CPC .. G02B 27/0172; G02B 27/017; G02B 27/01; A61B 3/112
USPC ........ 351/204, 221, 246; 345/619, 629, 632, 345/633, 158
See application file for complete search history.

(56) References Cited

U.S. PATENT DOCUMENTS 4,712,895 A * 12/1987 Kamiyama ............ A61B 3/113
                                                            351/204
7,174,094 B2    2/2007 Steinkamp
(Continued)

OTHER PUBLICATIONS

Wheelwright, Notice of Allowance, U.S. Appl. No. 15/583,952, dated Nov. 28, 2018, 9 pgs.
(Continued)

*Primary Examiner* — Hung X Dang
(74) *Attorney, Agent, or Firm* — Morgan, Lewis & Bockius LLP

(57) ABSTRACT

A head-mounted display device includes a first light element configured to transmit a first light having a first color; a second light element configured to transmit a second light having a second color; a first lens configured for directing the first light in a first direction and directing the second light in a second direction; and a first set of one or more lenses configured for directing the first light and the second light from the first lens toward a first eye of a user. Also disclosed is a method that includes transmitting a first light and a second light through a first lens and a first set of one or more lenses and directing the first light and the second light toward a first eye of a user. Further disclosed is a method for adjusting a position of one or more lenses.

20 Claims, 15 Drawing Sheets

(51) Int. Cl.
    *A61B 3/11*    (2006.01)
    *G02B 27/01*   (2006.01)

(56) References Cited

U.S. PATENT DOCUMENTS

2008/0198470 A1    8/2008    Hamilton
2016/0070103 A1    3/2016    Yoon

OTHER PUBLICATIONS

Wheelwright, Offfice Action, U.S. Appl. No. 15/583,962, dated Apr. 5, 2019, 24 pgs.
Wheelwright, Final Office Action, U.S. Appl. No. 15/583,962, dated Sep. 17, 2019, 30 pgs.

* cited by examiner

DEVICES AND METHODS FOR LENS ALIGNMENT BASED ON ENCODED COLOR PATTERNS

RELATED APPLICATION

This application is a continuation-in-part application of U.S. patent application Ser. No. 15/583,952, filed May 1, 2017, now U.S. Pat. No. 10,254,507, which is incorporated by reference herein in its entirety.

TECHNICAL FIELD

This relates generally to display devices, and more specifically to head-mounted display devices.

BACKGROUND

Head-mounted display devices (also called herein head-mounted displays) are gaining popularity as means for providing visual information to user. Different users can have different interpupillary distances, and it is important to set up a head-mounted display device for the correct interpupillary distance of a user, as an incorrect interpupillary distance can cause visual distortion.

However, determining an accurate interpupillary distance has often required professional assistance (e.g., a measurement by an optician). In the absence of such professional assistance, users often set up display devices for incorrect interpupillary distances, which reduces the quality of user experience with such devices.

SUMMARY

Accordingly, there is a need for an improved method and an improved device for adjusting an interpupillary distance, thereby improving the user experience with display devices.

The above deficiencies and other problems are reduced or eliminated by the disclosed devices and methods.

In accordance with some embodiments, a device includes a first light source device configured to transmit a first light in a first direction and a second light in a second direction that is distinct from the first direction; and a first set of one or more lenses configured for directing the first light and the second light from the first light source device toward a first eye of a user. The first light is spatially offset from the second light and one or more of the first light and the second light provide a cue for adjusting a location of the first set of one or more lenses.

In accordance with some embodiments, a method includes transmitting a first light in a first direction and a second light that is distinct from the first light in a second direction that is distinct from the first direction; and transmitting the first light and the second light through a first set of one or more lenses and directing the first light and the second light toward a first eye of a user. The first light is spatially offset from the second light and one or more of the first light and the second light provide a cue for adjusting a location of the first set of one or more lenses.

In accordance with some embodiments, a method includes receiving a portion of a bundle of light that includes a first light and a second light that is distinct from the first light and laterally offset from the first light; and, in accordance with a determination that the received portion of the bundle of light corresponds to the first light, moving the first set of one or more lenses.

In accordance with some embodiments, a head-mounted display device includes a first light source device that includes a first light element configured to transmit a first light having a first color; a second light element configured to transmit a second light having a second color that is distinct from the first color, the second light element being distinct and separate from the first light element; and a first lens configured for directing the first light from the first light element in a first direction and directing the second light from the second light element in a second direction that is distinct from the first direction. The device also includes a first set of one or more lenses configured for directing the first light and the second light from the first lens toward a first eye of a user.

In accordance with some embodiments, a method includes transmitting, to a first lens from a first light element, a first light having a first color; transmitting, to the first lens from a second light element that is distinct and separate from the first light element, a second light having a second color that is distinct from the first color; directing, with the first lens, the first light from the first light element in a first direction and the second light from the second light element in a second direction that is distinct from the first direction; and directing, with a first set of one or more lenses, the first light and the second from the first lens toward a first eye of a user.

In accordance with some embodiments, a method includes receiving, with a first eye of a user, a portion of a first bundle of light that includes a first light and a second light that is distinct from the first light and laterally offset from the first light, the first light and the second light having been transmitted through a first set of one or more lenses; and, in accordance with a determination that the received portion of the bundle of light corresponds to the second light, adjusting a position of the first set of one or more lenses.

Thus, the disclosed embodiments provide devices and methods that facilitate accurate determination and/or adjustment of interpupillary distances.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIG. 1O is a perspective view of a device in accordance with some embodiments.

Figure 1A:
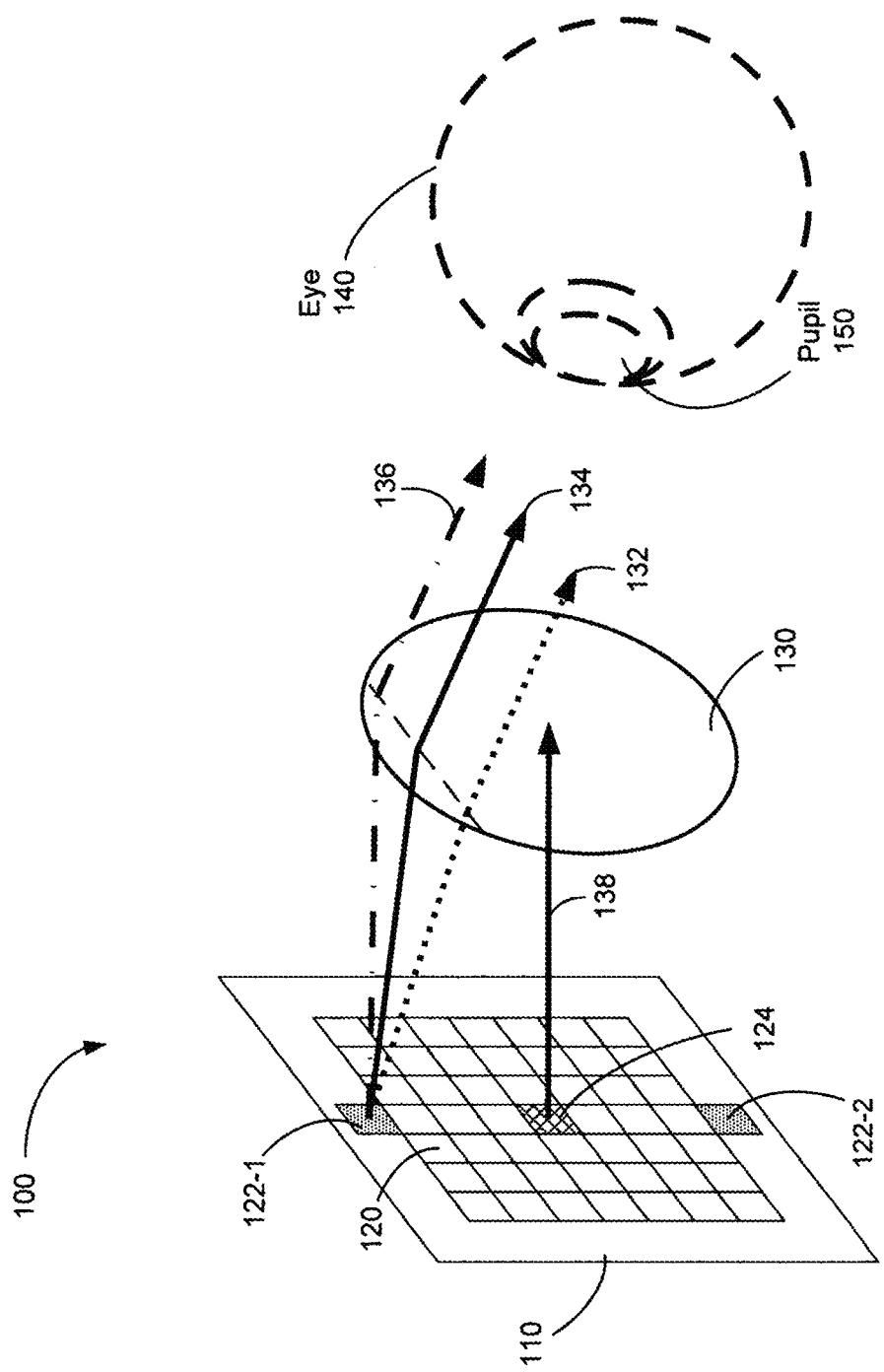
FIG. 1A is a schematic diagram of a device for determining and/or adjusting an offset of a lens in accordance with some embodiments.

These figures are not drawn to scale unless indicated otherwise.

DETAILED DESCRIPTION

Many viewing optics (e.g., eyeglasses, head-mounted display devices, etc.) require a correct positioning of the viewing optics relative to a position of an eye. Incorrect positioning of viewing optics can cause visual distortion. However, determining an accurate interpupillary distance has often required professional assistance (e.g., a measurement by an optician). In the absence of such professional assistance, users can set up viewing optics for incorrect interpupillary distances. For example, users may be asked to adjust lateral positions of lenses until a crosshair appears the sharpest. Certain users may not be able to accurately determine when the crosshair appears the sharpest.

The disclosed device, including a light source device coupled with one or more lenses, allows accurate determination and/or adjustment of an interpupillary distance utilizing a projection of an encoded light pattern.

In some embodiments, the light source device and the one or more lenses are included in a head-mounted display device, which is, in turn, used for providing virtual reality and/or augmented reality content. In some embodiments, the light source device and the one or more lenses are included in a stand-alone diagnostic device for determining an interpupillary distance.

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are used only to distinguish one element from another. For example, a first lens could be termed a second lens, and, similarly, a second lens could be termed a first lens, without departing from the scope of the various described embodiments. The first lens and the second lens are both lenses, but they are not the same lens.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof. The term "exemplary" is used herein in the sense of "serving as an example, instance, or illustration" and not in the sense of "representing the best of its kind."

FIG. 1A is an isometric view of display device 100 in accordance with some embodiments. In some other embodiments, display device 100 is part of some other electronic display (e.g., head-mounted displays, digital microscope, etc.). In some embodiments, display device 100 includes light emission device array 110 and one or more lenses (e.g., lens 130). Light emission device array 110 emits image light toward a viewing user.

In some embodiments, light emission device array 110 includes light emission devices 120 (e.g., pixels) that emit light in the visible light. For example, light emission device array 110 includes an array of light-emitting diodes (LEDs), an array of microLEDs, an array of OLEDs, or some combination thereof.

In some embodiments, light emission device array 110 includes one or more light sources (e.g., a fluorescent light source or a broadband light source, such as a white LED) and an emission intensity array. The emission intensity array is configured to selectively attenuate light emitted from the one or more light sources. In some embodiments, the emission intensity array is composed of a plurality of liquid crystal cells or pixels. Each of the liquid crystal cells is, or in some embodiments, groups of liquid crystal cells are, addressable to have specific levels of attenuation. For example, at a given time, some of the liquid crystal cells may be set to no attenuation, while other liquid crystal cells may be set to maximum attenuation. In this manner, the emission intensity array is able to control what portion of the image light emitted from the one or more light sources is passed to the one or more lenses (e.g., lens 130). In some embodiments, the one or more light sources include light emission devices 120, such as an array of LEDs, an array of microLEDs, an array of OLEDs, or a combination thereof One or more lenses (e.g., lens 130) receive light from emission device array 110, and direct the light to a location of pupil 150. In some embodiments, lens 130 includes one or more diffractive optics. In some embodiments, the one or more lenses include active lens. An active lens is a lens whose lens curvature and/or refractive ability may be dynamically controlled (e.g., via a change in applied voltage). An active lens may be a liquid crystal lens, a liquid lens (e.g., using electro-wetting), or some other lens whose curvature and/or refractive ability may be dynamically controlled, or some combination thereof. Accordingly, in some embodiments, system 200 (described with respect to FIG. 2) may dynamically adjust the curvature and/or refractive ability of active lenslets to direct light received from light emission device array 110 to pupil 150.

FIG. 1A also illustrates one or more light source devices 122 (e.g., light source device 122-1 and/or light source device 122-2) are located adjacent to light emission device array 110. In some embodiments, one or more light source devices 122 are integrated with light emission device array 110. In some embodiments, one or more light source devices 122 are separate from light emission device array 110, but one or more light source devices 122 are located in proximity to light emission device array 110 (e.g., one or more light source devices 122 are located on light emission device array 110). In some embodiments, light source device 122 (e.g., light source device 122-1 and/or light source device 122-2) is located adjacent to a top or bottom edge of light emission device array 110.

In some embodiments, light source device 122 (e.g., light source device 122-1 and/or light source device 122-2) is located adjacent to a center of a top or bottom edge of light emission device array 110. For example, in FIG. 1A, light source device 122-1 is located adjacent to a center of a top edge of light emission device array 110, and light source device 122-2 is located adjacent to a center of a bottom edge of light emission device array 110. In some embodiments, a light source device (e.g., light source device 122-1 or light source device 122-2) is located within at least 1 mm, 2 mm, 3 mm, 4 mm, or 5 mm from a center of a top or bottom edge of light emission device array 110. In some embodiments, the device provides to a user instructions to look toward light source device 122 (e.g., look up or look down, depending on the location of light source device 122).

In FIG. 1A, light source device 122-1 emits first light 132 (e.g., a red light) in a first direction, second light 134 (e.g., a green light) in a second direction, and third light 136 (e.g., a blue light) in a third direction. First light 132, second light 134, and third light 136 are spatially separated. In some cases, only one of first light 132, second light 134, and third light 136 enters through pupil 150 of eye 140 depending on a position of eye 140 (e.g., a position of pupil 150 of eye 140). Thus, the projection of first light 132, second light 134, and third light 136 can be used to determine whether lens 130 is aligned with eye 140.

In some embodiments, light emission device array 110 also displays additional features for assisting a user with determining whether lens 130 is aligned with eye 140. In FIG. 1A, one or more light emission devices 120 (e.g., pixels) of light emission device array 110 optionally emit reference light 138. In some embodiments, reference light 138 corresponds to second light 134 (e.g., reference light 138 has a same color and/or a same pulsing frequency as second light 134) so that reference light 138 can serve as a guide for determining whether lens 130 is aligned with eye 140. In some embodiments, light emission device array 110 optionally displays instructions for guiding users in adjusting the position of lens 130.

Figure 1B:
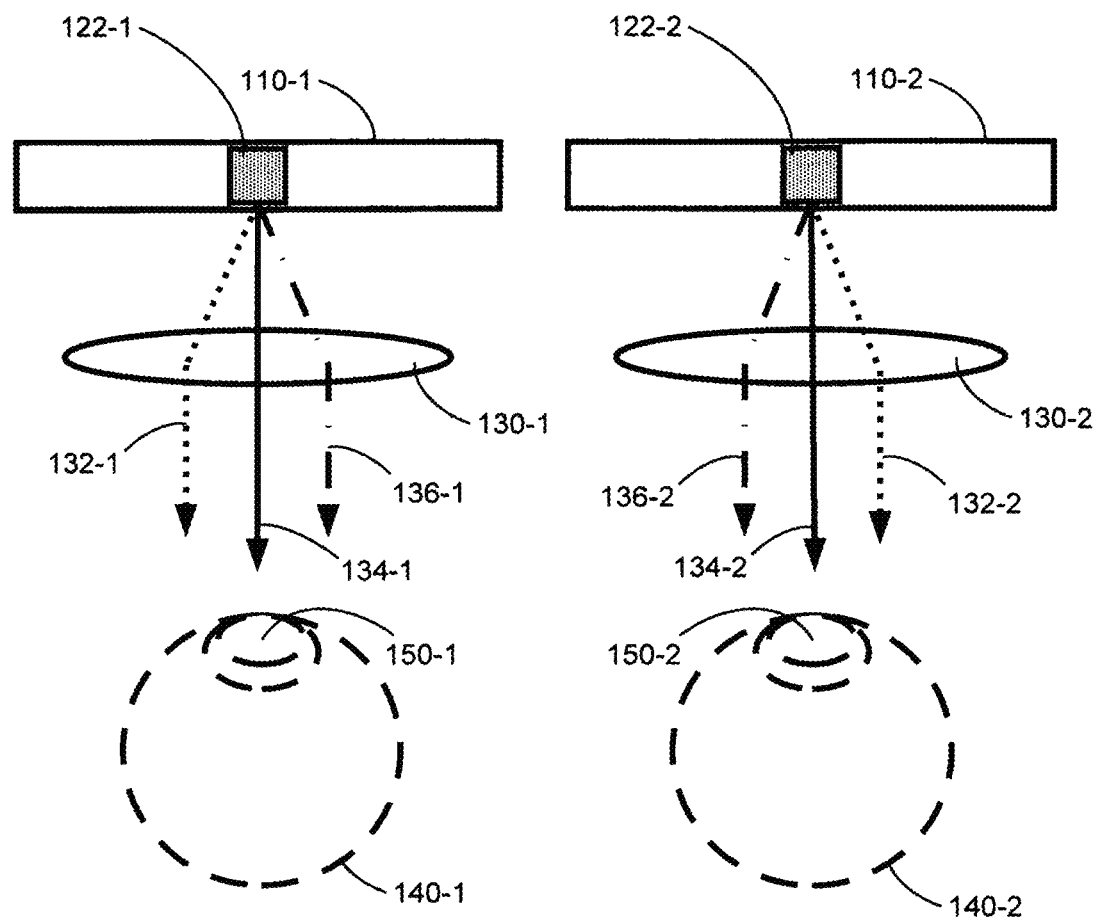
FIG. 1B is a schematic diagram illustrating an example configuration where lenses are aligned with eyes.

FIG. 1B is a schematic diagram illustrating an example configuration (e.g., an example plan view) where lenses are aligned with eyes.

In FIG. 1B, the device includes light source device 122-1 and light source device 122-2. In some embodiments, light source device 122-1 is coupled with light emission device array 110-1 (e.g., a display screen) and light source device 122-2 is coupled with light emission device array 110-2 (e.g., a display screen). In some embodiments, light source device 122-1 is located adjacent to a lateral center of light emission device array 110. In some embodiments, light source device 122-1 is located adjacent to a lateral center of a top or bottom edge of light emission device array 110.

Light source device 122-1 emits first light 132-1 (e.g., a red light) in a first direction, second light 134-1 (e.g., a green light) in a second direction, and third light 136-1 (e.g., a blue light) in a third direction. First light 132-1, second light 134-1, and third light 136-1 from light source device 122-1 are transmitted through lens 130-1, which direct first light 132-1, second light 134-1, and third light 136-1 toward eye 140-1 (e.g., a left eye). For example, first light 132-1, second light 134-1, and third light 136-1 are collimated after passing through lens 130-1. In some embodiments, light source device 122-1 is located at a focal plane of lens 130-1. As shown in FIG. 1B, first light 132-1 is spatially separated from second light 134-1 and third light 136-1, and second light 134-1 is spatially separated from third light 136-1, after passing through lens 130-1. In some embodiments, first light 132-1 is parallel to second light 134-1 and third light 136-1 after passing through lens 130-1. In some embodiments, first light 132-1 is spatially offset from second light 134-1 by at least 1 mm, 2 mm, 3 mm, 4 mm, 5 mm, 6 mm, 7 mm, 8 mm, 9 mm, or 10 mm. In some embodiments, second light 134-1 is spatially offset from third light 136-1 by at least 1 mm, 2 mm, 3 mm, 4 mm, 5 mm, 6 mm, 7 mm, 8 mm, 9 mm, or 10 mm.

Similarly, light source device 122-2 emits fourth light 132-2 (e.g., a red light) in a fourth direction, fifth light 134-2 (e.g., a green light) in a fifth direction, and sixth light 136-2 (e.g., a blue light) in a sixth direction. Fourth light 132-2, fifth light 134-2, and sixth light 136-2 from light source device 122-2 are transmitted through lens 130-2, which direct fourth light 132-2, fifth light 134-2, and sixth light 136-2 toward eye 140-2 (e.g., a right eye). For example, fourth light 132-2, fifth light 134-2, and sixth light 136-2 are collimated after passing through lens 130-2. In some embodiments, light source device 122-2 is located at a focal plane of lens 130-2. As shown in FIG. 1B, fourth light 132-2 is spatially separated from fifth light 134-2 and sixth light 136-2, and fifth light 134-2 is spatially separated from sixth light 136-2, after passing through lens 130-2. In some embodiments, fourth light 132-2 is parallel to fifth light 134-2 and sixth light 136-2 after passing through lens 130-2. In some embodiments, fourth light 132-2 is spatially offset from fifth light 134-2 by at least 1 mm, 2 mm, 3 mm, 4 mm, 5 mm, 6 mm, 7 mm, 8 mm, 9 mm, or 10 mm. In some embodiments, fifth light 134-2 is spatially offset from sixth light 136-2 by at least 1 mm, 2 mm, 3 mm, 4 mm, 5 mm, 6 mm, 7 mm, 8 mm, 9 mm, or 10 mm.

In FIG. 1B, a lateral position of eye 140-1 is aligned with a lateral position of lens 130-1 (e.g., a lateral position of an optical center of lens 130-1), and second light 134-1 (e.g., a green light) enters through pupil 150-1 of eye 140-1. In addition, a lateral position of eye 140-2 is aligned with a lateral position of lens 130-2 (e.g., a lateral position of an optical center of lens 130-2), and fifth light 134-2 (e.g., a green light) enters through pupil 150-2 of eye 140-2. FIG. 1B also shows that first light 132-1 (e.g., a red light) and third light 136-1 (e.g., a blue light) do not enter through pupil 150-1 of eye 140-1, and fourth light 132-2 (e.g., a red light) and sixth light 136-2 (e.g., a blue light) do not enter through pupil 150-2 of eye 140-2. Second light 134-1 (e.g., a green light) received with eye 140-1 indicates that a lateral position of lens 130-1 is aligned with a lateral position of eye 140-1 and fifth light 134-2 (e.g., a green light) received with eye 140-2 indicates that a lateral position of lens 130-2 is aligned with a lateral position of eye 140-2. Thus, no adjustment of the lateral position of lens 130-1 or the lateral position of lens 130-2 is necessary.

Figure 1C:
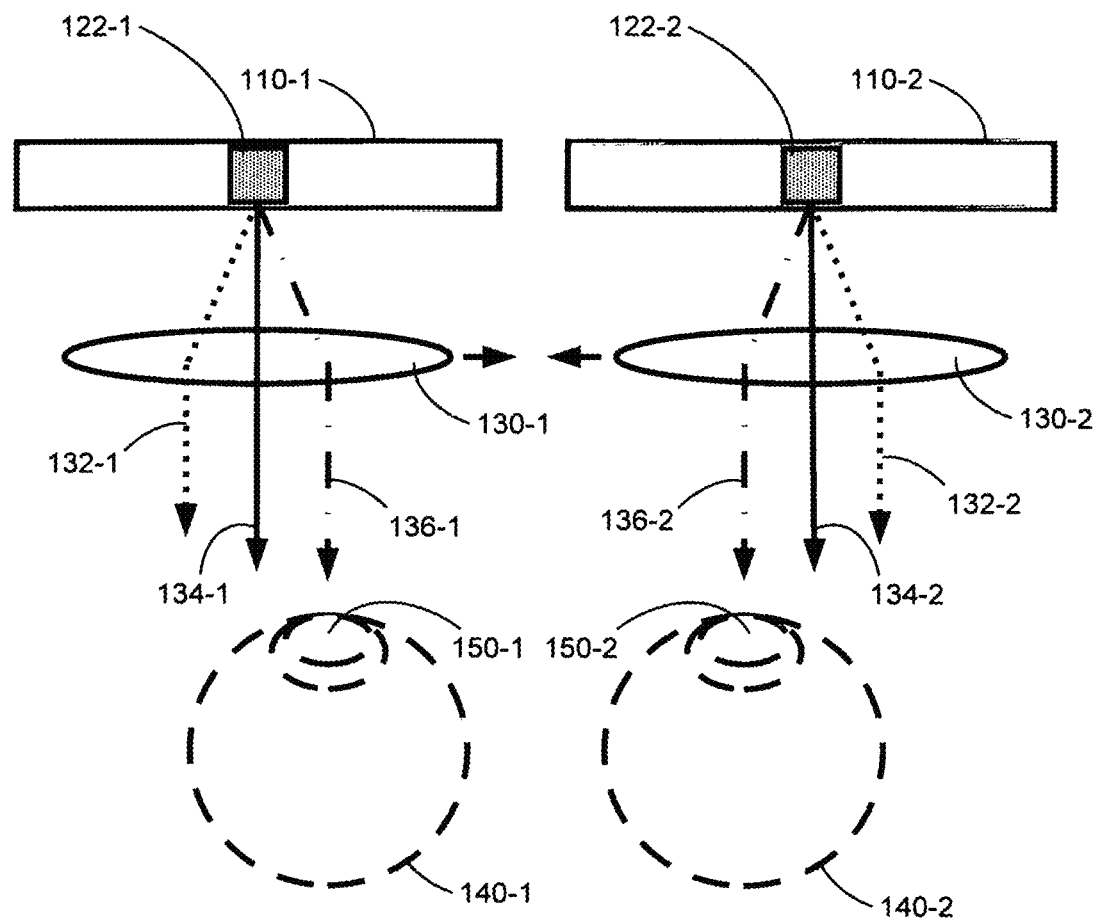
FIGS. 1C-1E are schematic diagrams illustrating example configurations where lenses are not aligned with eyes.
Figure 1D:
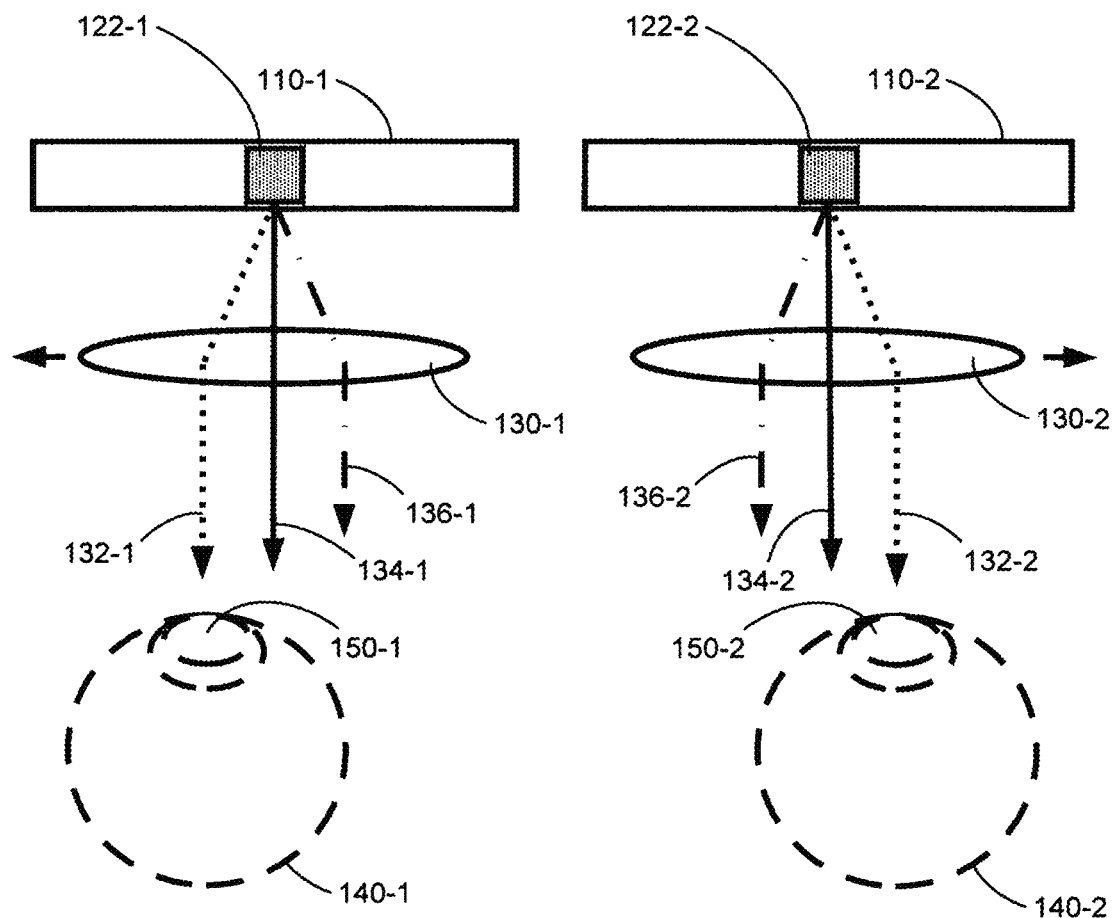
Figure 1E:
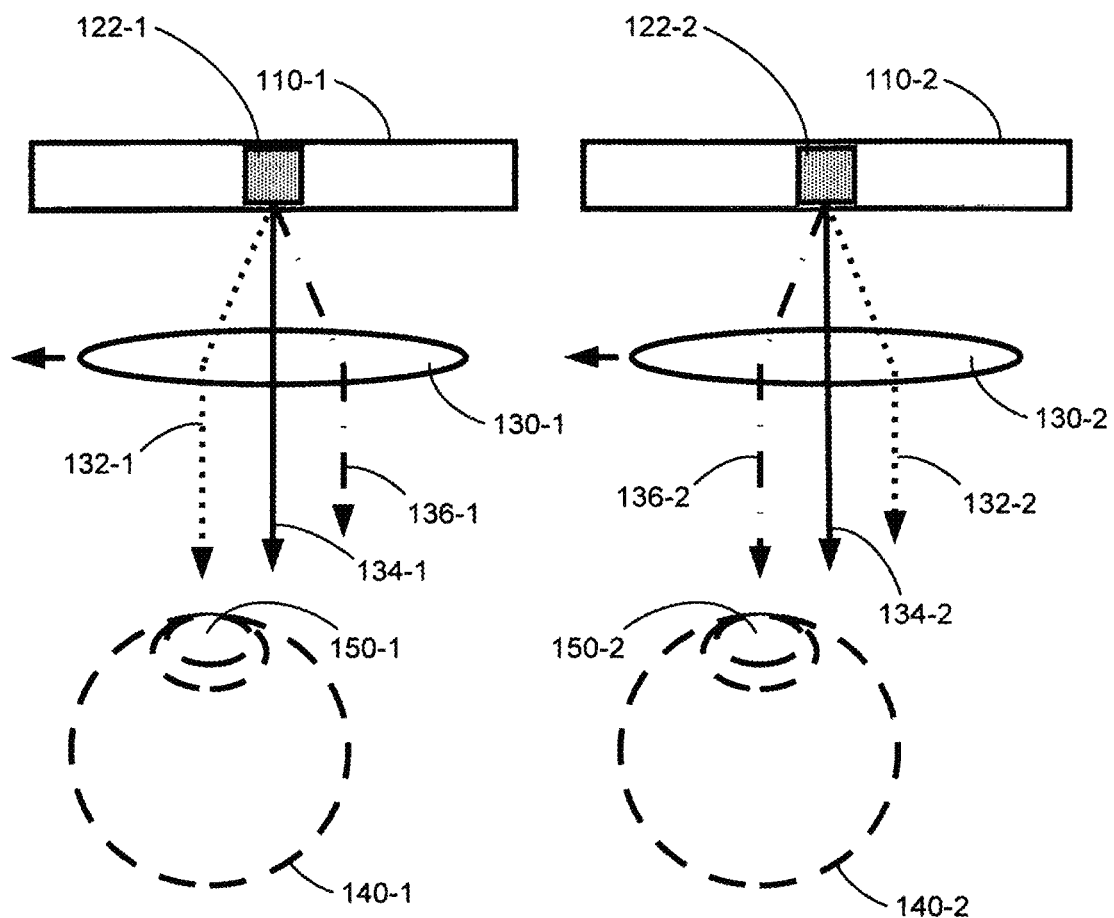

FIGS. 1C-1E are schematic diagrams illustrating example configurations where lenses are not aligned with eyes.

In FIG. 1C, third light 136-1 (e.g., a blue light) enters through pupil 150-1 of eye 140-1. In addition, sixth light 136-2 (e.g., a blue light) enters through pupil 150-2 of eye 140-2. FIG. 1C also shows that first light 132-1 (e.g., a red light) and second light 134-1 (e.g., a green light) do not enter through pupil 150-1 of eye 140-1, and fourth light 132-2 (e.g., a red light) and fifth light 134-2 (e.g., a green light) do not enter through pupil 150-2 of eye 140-2. Third light 136-1 (e.g., a blue light) received with eye 140-1 indicates that a lateral position of lens 130-1 is located on the left side of a lateral position of eye 140-1, and sixth light 136-2 (e.g., a blue light) received with eye 140-2 indicates that a lateral position of lens 130-2 is located on the right side of a lateral position of eye 140-2.

When lens 130-1 and lens 130-2 are included in a head-mounted display device, this indicates that the head-mounted display device is configured for an interpupillary distance shorter than the interpupillary distance of the user. Thus, the user can adjust the distance between lens 130-1 and lens 130-2 (e.g., increasing an interpupillary distance setting for the head-mounted display device) until second light 134-1 (e.g., a green light) is received with eye 140-1 and fifth light 134-2 (e.g., a green light) is received with eye 140-2, as shown in FIG. 1B.

In FIG. 1D, first light 132-1 (e.g., a red light) enters through pupil 150-1 of eye 140-1. In addition, fourth light 132-2 (e.g., a red light) enters through pupil 150-2 of eye 140-2. FIG. 1D also shows that second light 134-1 (e.g., a green light) and third light 136-1 (e.g., a blue light) do not enter through pupil 150-1 of eye 140-1, and fifth light 134-2 (e.g., a green light) and sixth light 136-2 (e.g., a blue light) do not enter through pupil 150-2 of eye 140-2. First light 132-1 (e.g., a red light) received with eye 140-1 indicates that a lateral position of lens 130-1 is located on the right side of a lateral position of eye 140-1, and fourth light 132-2 (e.g., a red light) received with eye 140-2 indicates that a lateral position of lens 130-2 is located on the left side of a lateral position of eye 140-2.

When lens 130-1 and lens 130-2 are included in a head-mounted display device, this indicates that the head-mounted display device is configured for an interpupillary distance longer than the interpupillary distance of the user. Thus, the user can adjust the distance between lens 130-1 and lens 130-2 (e.g., decreasing an interpupillary distance setting for the head-mounted display device) until second light 134-1 (e.g., a green light) is received with eye 140-1 and fifth light 131 2 (e.g., a green light) is received with eye 140-2, as shown in FIG. 1B.

In FIG. 1E, first light 132-1 (e.g., a red light) enters through pupil 150-1 of eye 140-1. In addition, sixth light 132-2 (e.g., a blue light) enters through pupil 150-2 of eye 140-2. FIG. 1E also shows that second light 134-1 (e.g., a green light) and third light 136-1 (e.g., a blue light) do not enter through pupil 150-1 of eye 140-1, and fourth light 132-2 (e.g., a red light) and fifth light 134-2 (e.g., a green light) do not enter through pupil 150-2 of eye 140-2. First light 132-1 (e.g., a red light) received with eye 140-1 indicates that a lateral position of lens 130-1 is located on the right side of a lateral position of eye 140-1, and sixth light 132-2 (e.g., a blue light) received with eye 140-2 indicates that a lateral position of lens 130-2 is located on the right side of a lateral position of eye 140-2.

When lens 130-1 and lens 130-2 are included in a head-mounted display device, this indicates that the head-mounted display device is positioned off toward a right side of the user. Thus, the user can reposition the head-mounted display device on the user's head (e.g., push the head-mounted display device toward a left side of the user's head) until second light 134-1 (e.g., a green light) is received with eye 140-1 and fifth light 134-2 (e.g., a green light) is received with eye 140-2, as shown in FIG. 1B.

Although FIGS. 1B-1E illustrate that the fourth direction corresponds to the third direction and the sixth direction corresponds to the first direction (e.g., for each lens, the red light is projected toward an outside of the head-mounted display and the blue light is projected toward an inside of the head-mounted display), in some embodiments, the fourth direction corresponds to the first direction and the sixth direction corresponds to the third direction (e.g., for each lens, the red light is projected toward a left side of the head-mounted display and the blue light is projected toward a right side of the head-mounted display).

Although FIGS. 1B-1E described that first light 132-1, second light 134-1, third light 136-1, fourth light 132-2, fifth light 134-2, and sixth light 136-2 have certain colors, additionally or alternatively, first light 132-1, second light 134-1, third light 136-1, fourth light 132-2, fifth light 134-2, and sixth light 136-2 have a respective time-dependent intensity pattern (e.g., a pulsing frequency, a duty cycle, and/or an interval). For example, first light 132-1 has a first pulsing frequency (e.g., first light 132-1 pulses at the first pulsing frequency), second light 134-1 has a second pulsing frequency (e.g., second light 134-1 pulses at the second pulsing frequency), third light 136-1 has a third pulsing frequency (e.g., third light 136-1 pulses at the third pulsing frequency), fourth light 132-2 has a fourth pulsing frequency (e.g., fourth light 132-2 pulses at the fourth pulsing frequency), fifth light 134-2 has a fifth pulsing frequency (e.g., fifth light 134-2 pulses at the fifth pulsing frequency), and sixth light 136-2 has a sixth pulsing frequency (e.g., sixth light 136-2 pulses at the sixth pulsing frequency). The pulsing frequencies of first light 132-1, second light 134-1, third light 136-1, fourth light 132-2, fifth light 134-2, and sixth light 136-2 can be used to determine whether lens 130-1 is aligned with eye 140-1 and lens 130-2 is aligned with eye 140-2.

In some embodiments, the device illustrated in FIGS. 1B-1E is used to determine an interpupillary distance (e.g., the interpupillary distance is determined from the positions of lenses 130-1 and 130-2 when both lenses 130-1 and 130-2 are aligned with eyes 140-1 and 140-2). Thus, in some embodiments, the device can be used as a device for measuring an interpupillary distance. In some embodiments, the device is included in, and/or coupled with, another optical device (e.g., a head-mounted display device as shown in FIG. 1O, an optical microscope, binoculars, etc.) to adjust the optical device to match the interpupillary distance.

In addition, although FIGS. 1B-1E illustrate adjusting positions of two lenses (e.g., adjusting an interpupillary distance, which frequently involves moving both lenses), it is possible to use an analogous method for adjusting a position of a single lens of a single lens system (e.g., a display system configured to operate with a single eye only), or separately adjusting a position of an individual lens of a multi-lens system.

Although FIGS. 1B-1E illustrate the use of six light components (e.g., first light 132-1, second light 134-1, third light 136-1, fourth light 132-2, fifth light 134-2, and sixth light 136-2), in some embodiments, fewer or more light components can be used. For example, in some embodiments, both the first light and the third light have a same color (e.g., red) and the third light has a distinct color (e.g., green). In such embodiments, a light source device does not need to emit a light of a third color (e.g., a blue light). Thus, in some cases, a light of a first color (e.g., a green light) received with eye 140-1 indicates that a lateral position of lens 130-1 is aligned with a lateral position of eye 140-1, and a light of a second color (e.g., a red light) received with eye 140-1 indicates that a lateral position of lens 130-1 is not aligned with a lateral position of eye 140-1 without indicating a direction of the misalignment (or in which direction lens 130-1 should move to match the lateral position of eye 140-1). In some embodiments, light source device 122-1 emits light of four or more colors. This provides an additional resolution in adjusting the lateral position of lens 130-1. In some embodiments, light source device 122-1 emits light having a continuous spectrum of colors as described below with FIGS. 1H-1I.

FIGS. 1F-1I are schematic diagrams illustrating example light source devices in accordance with some embodiments.

Figure 1F:
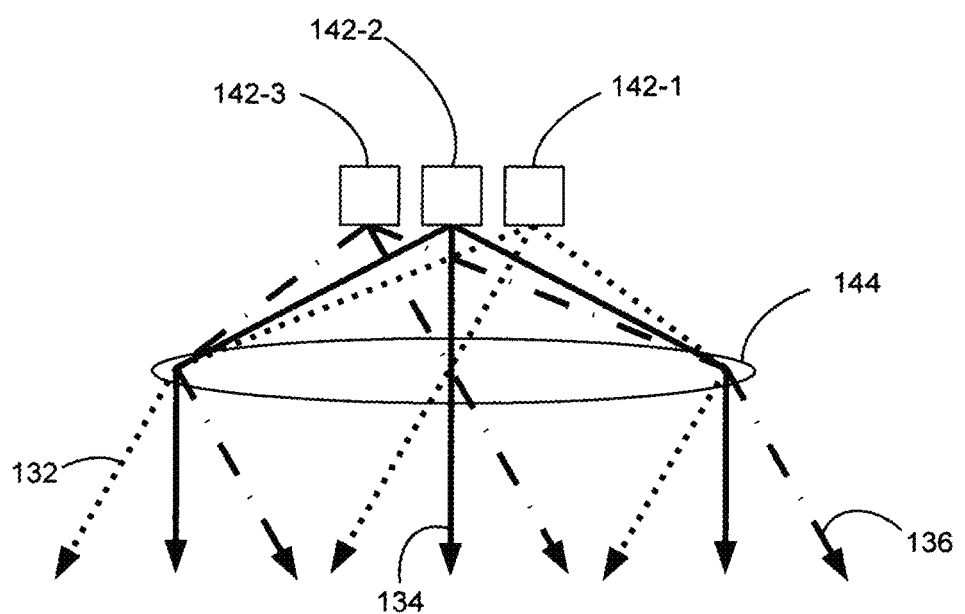
FIGS. 1F-1I are schematic diagrams illustrating example light source devices in accordance with some embodiments.

FIG. 1F shows a light source device that includes first light emitting component 142-1, second light emitting component 142-2, and third light emitting component 142-3. In some embodiments, each light emitting component is an LED, an organic LED (OLED), an array of LED and/or OLED, or a combination thereof.

In some embodiments, the light source device includes more or fewer light emitting components. First light emitting component 142-1 is configured to emit a first light, second light emitting component 142-2 is configured to emit a second light, and third light emitting component 142-3 is configured to emit a third light. In some embodiments, the first light has a first color (e.g., red) and/or a first time-dependent intensity pattern (e.g., a first pulsing frequency, a first duty cycle, and/or a first interval), the second light has a second color (e.g., green) and/or a second time-dependent intensity pattern (e.g., a second pulsing frequency, a second duty cycle, and/or a second interval), and the third light has a third color (e.g., blue) and/or a third time-dependent intensity pattern (e.g., a third pulsing frequency, a third duty cycle, and/or a third interval).

In some embodiments, first light emitting component 142-1, second light emitting component 142-2, and third light emitting component 142-3 are positioned on a focal plane of lens 144, as shown in FIG. 1F. In addition, first light emitting component 142-1, second light emitting component 142-2, and third light emitting component 142-3 are laterally offset from one another.

In some embodiments, lens 144 is rotationally symmetric (e.g., lens 144 is a spherical lens). In some embodiments, lens 144 is reflectionally symmetric (e.g., lens 144 is a cylindrical lens). In some embodiments, lens 144 is a two-dimensional lens (e.g., lens 144 is a spherical lens). In some embodiments, lens 144 is a one-dimensional lens (e.g., lens 144 is a cylindrical lens).

FIG. 1F also shows that first light emitting component 142-1 emits light in multiple directions, and the light from first light emitting component 142-1 is directed to a first direction after passing through lens 144. Second light emitting component 142-2 emits light in multiple directions, and the light from second light emitting component 142-2 is directed to a second direction after passing through lens 144. Third light emitting component 142-3 emits light in multiple directions, and the light from third light emitting component 142-3 is directed to a third direction after passing through lens 144. Thus, the light emitting device shown in FIG. 1F is configured to transmit first light 132 in a first direction, second light 134 in a second direction, and third light 136 in a third direction.

Figure 1G:
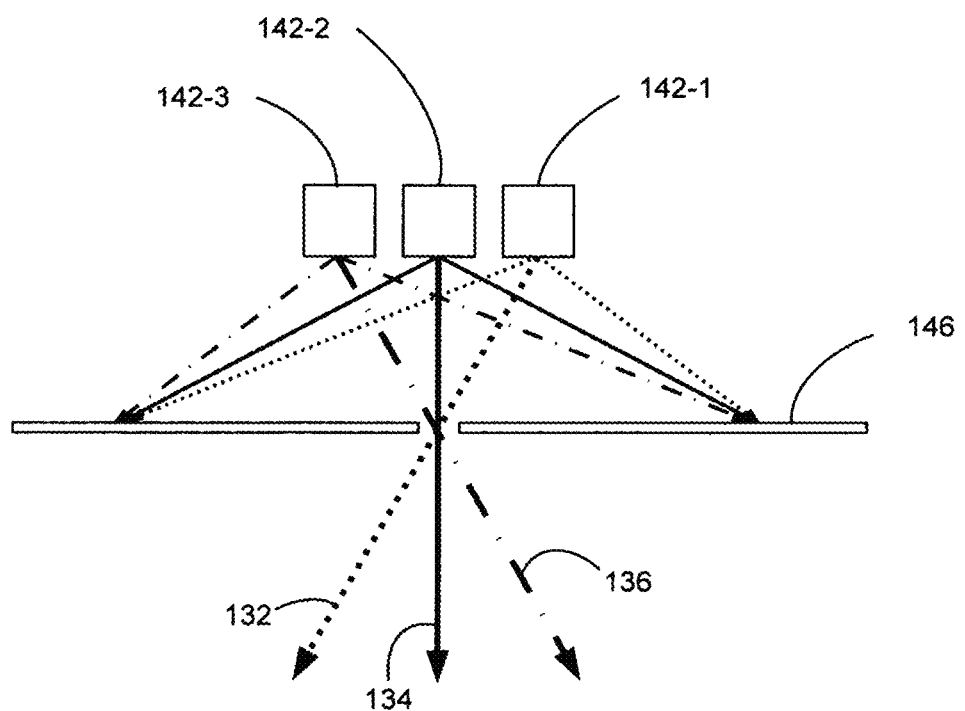

FIG. 1G shows a light source device that includes first light emitting component 142-1, second light emitting component 142-2, and third light emitting component 142-3. First light emitting component 142-1, second light emitting component 142-2, and third light emitting component 142-3 are described above with respect to FIG. 1F.

The light source device includes barrier 146 with an opening. In some embodiments, the opening is a pinhole. In some embodiments, the opening is a slit. The opening of barrier 146 transmits light having a particular direction from each light emitting component. For example, light from first light emitting component 142-1 that is not directed to the opening is blocked by barrier 146. Thus, the light emitting device shown in FIG. 1G is configured to transmit first light 132 in a first direction, second light 134 in a second direction, and third light 136 in a third direction.

Figure 1H:
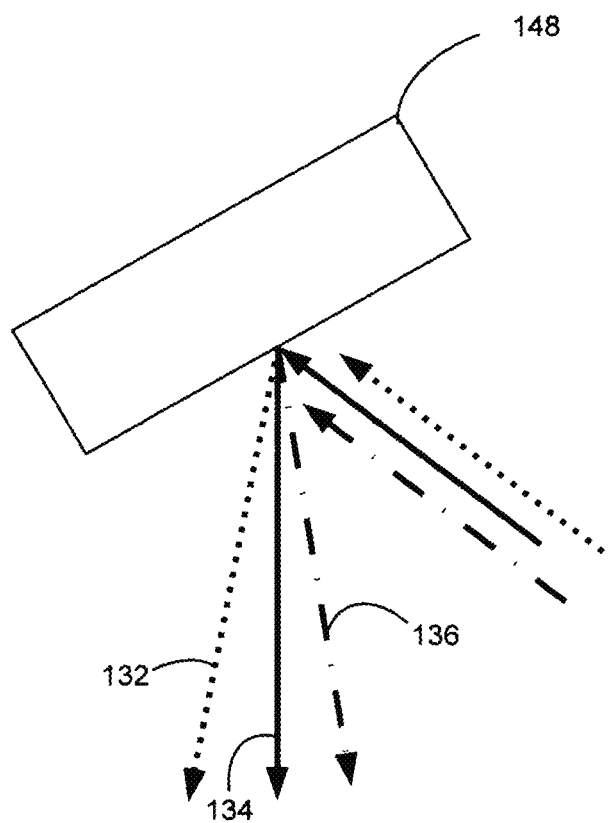

FIG. 1H shows a light source device that includes optical grating 148. In FIG. 1H, optical grating 148 receives a light that includes multiple color components (e.g., the light includes two or more of a red light component, a green light component or a blue light component). In some embodiments, the light source device receives a white light. Optical grating 148 disperses the light components based on their respective wavelengths. For example, as shown in FIG. 1H, optical grating 148 disperses first light 132 into a first direction, second light 134 into a second direction, and third light 136 into a third direction. In some embodiments, the light source device also includes a light source configured to provides the light with multiple color components (e.g., a broadband light source, such as an incandescent bulb, and a superluminescent light emitting diode, or a combination of multiple colored light emitting components shown in FIG. 1F).

Figure 1I:
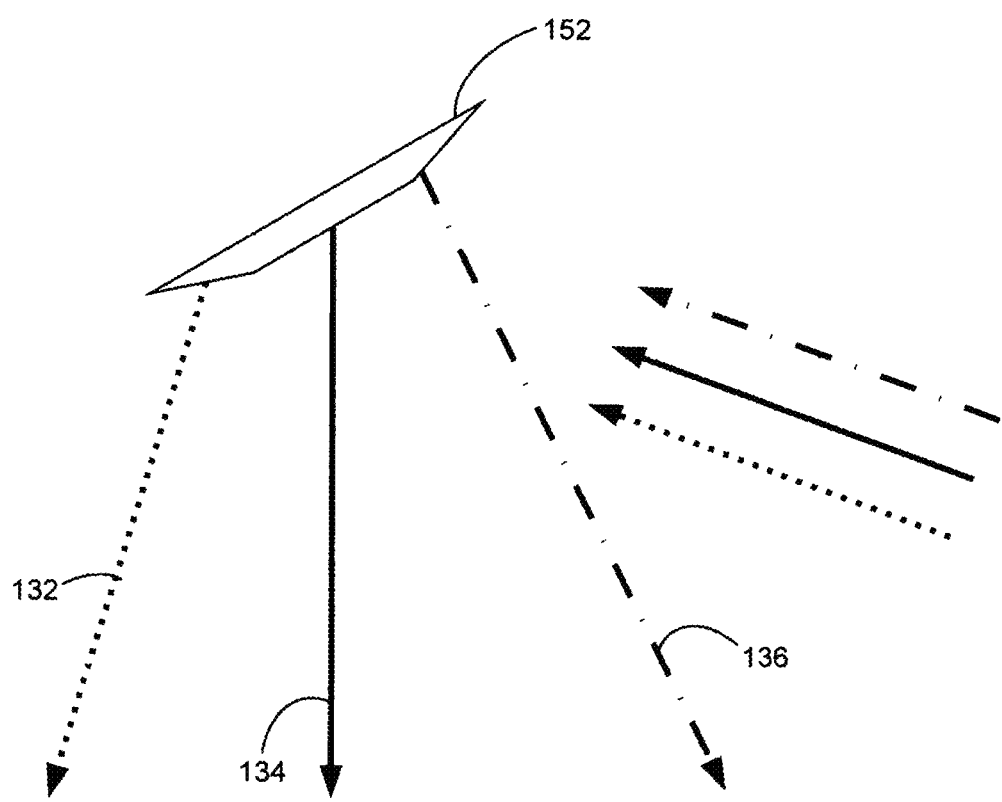

FIG. 1I is similar to FIG. 1H, except that set 152 of dichroic mirrors is used. In some embodiments, set 152 of dichroic mirrors include a single multi-faceted component, where each dichroic mirror is located on a respective facet. Each dichroic mirror is configured to reflect a light having a particular wavelength (or a range of wavelengths). Thus, the light emitting device shown in FIG. 1G is configured to direct first light 132 in a first direction, second light 134 in a second direction, and third light 136 in a third direction.

The light source devices shown in FIGS. 1F-1I can be used as described above with respect to FIGS. 1A-1E for determining and/or adjusting an alignment of one or more lenses.

Figure 1J:
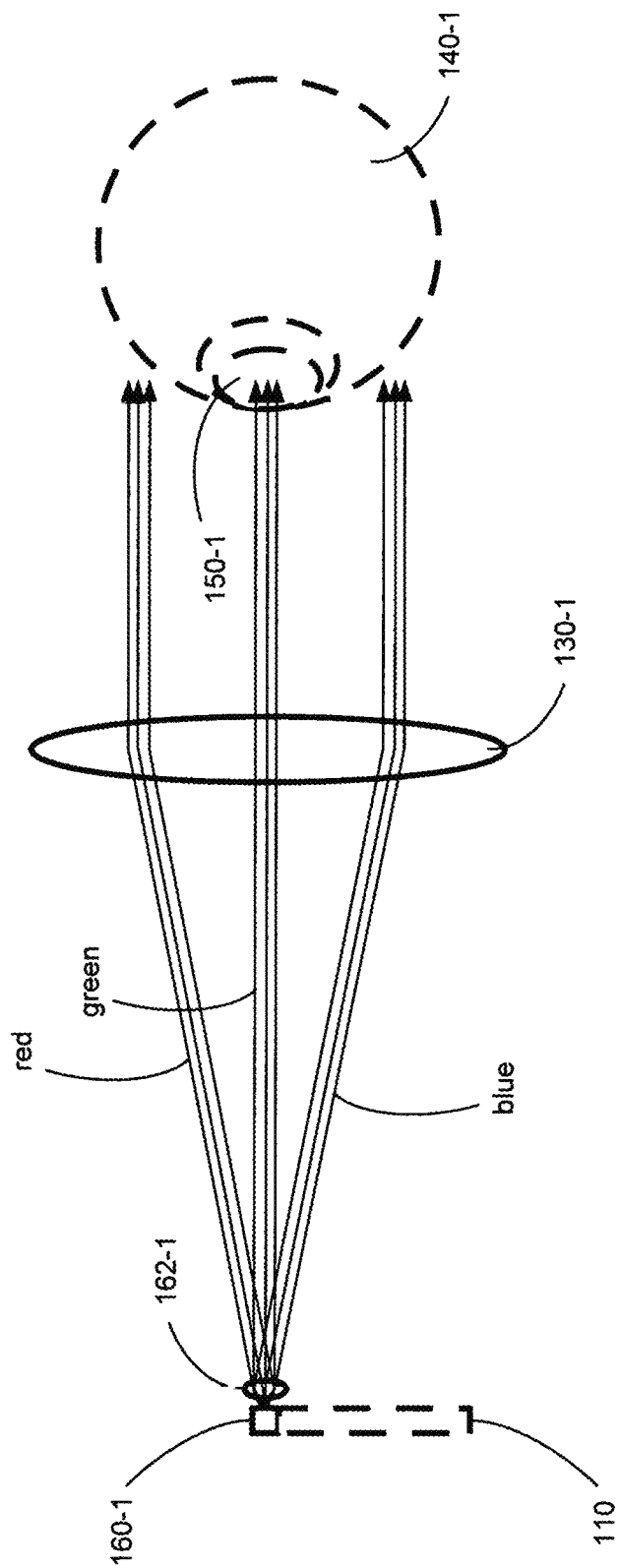
FIG. 1J is a schematic, diagram illustrating an example device in accordance with some embodiments.

FIG. 1J is a schematic diagram illustrating an example device in accordance with some embodiments.

In FIG. 1J, a device includes array 160-1 of light elements (e.g., pixels or subpixels). In some embodiments, array 160-1 of light elements is located adjacent to light emission device array 110 (which is configured for displaying images and/or videos) as shown in FIG. 1J. In some embodiments, array 160-1 of light elements is separate and distinct from light emission device array 110.

Array 160-1 of light elements includes two or more light elements-(e.g., two light elements, three light elements, four light elements, five light elements, etc.). In FIG. 1J, array 160-1 of light elements includes a first light element, a second light element, and a third light element. The first light element is configured for transmitting a first light having a first color (e.g., green), the second light element is configured for transmitting a second light having a second color (e.g., red), and the third light element is configured for transmitting a third light having a third color (e.g., blue).

The device also includes lens 162-1 (e.g., a microlens). Lens 162-1 is typically sized to cover multiple light elements (e.g., two pixels or subpixels, three pixels or subpixels, four pixels or subpixels, five pixels or subpixels, etc.). Lens 162-1 is configured for directing the first light (e.g., green light) in a first direction, the second light (e.g., red light) in a second direction, and the third light (e.g., blue light) in a third direction. In some embodiments, when array 160-1 of light elements is located adjacent to light emission device array 110, lens 162-1 is configured (e.g., sized and positioned) so as not to interact with light from light emission device array 110. In some embodiments, lens 162-1 has a representative width (e.g., a diameter in case of a circular lens, or a width in case of a rectangular lens) 1 mm or less, such as 1 mm, 0.9 mm, 0.8 mm, 0.7 mm, 0.6 mm, 0.5 mm, 0.4 mm, 0.3 mm, 0.2 mm, or 0.1 mm.

The device further includes first set 130-1 of one or more lenses configured for directing light from lens 162-1 toward eye 140-1 of a user. In some embodiments, first set 130-1 of one or more lenses are also configured for directing light from light emission device array 110 toward eye 140-1 of the user.

As shown in FIG. 1J, based on a position of eye 140-1 (and more specification a position of entrance pupil 150-1 of eye 140-1), only a portion of light from light elements is transmitted through entrance pupil 150-1 of eye 140-1. For example, when lens 130-1 is aligned with entrance pupil 150-1, green light is transmitted through entrance pupil 150-1. When lens 130-1 is located above entrance pupil 150-1 (or entrance pupil 150-1 is located below an optical axis of lens 130-1), blue light is transmitted through entrance pupil 150-1. When lens 130-1 is located below entrance pupil 150-1 (or entrance pupil 150-1 is located above an optical axis of lens 130-1), red light is transmitted through entrance pupil 150-1. Thus, based on a color of the transmitted light, the user can determine whether lens 130-1 is aligned with eye 140-1. When lens 130-1 is not aligned with eye 140-1, the user adjusts a position of lens 130-1 until lens 130-1 is aligned with eye 140-1.

Although FIG. 1J illustrates the device with components for one eye, in some embodiments, the device includes components for two eyes (e.g., the device includes a second array of light elements, a second lens, and a second set of one or more lenses). A person having ordinary skill in the art would understand that the second array of light elements has structures corresponding to the structures of array 160-1 of light elements, the second lens has structures corresponding to the structures of lens 162-1, and the second set of one or more lenses has structures corresponding to the structures of first set 130-1 of one or more lenses. For brevity, such details are omitted herein.

Figure 1K:
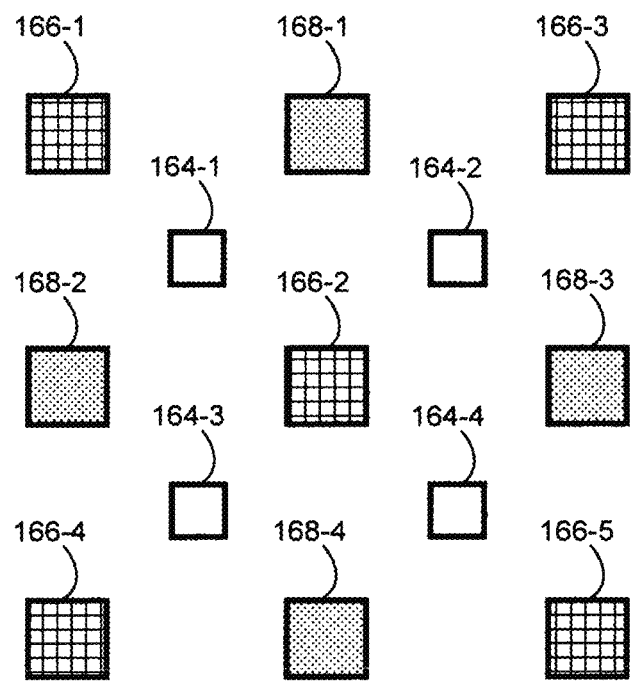
FIG. 1K and 1L are schematic diagrams illustrating light elements in accordance with some embodiments.
Figure 1L:
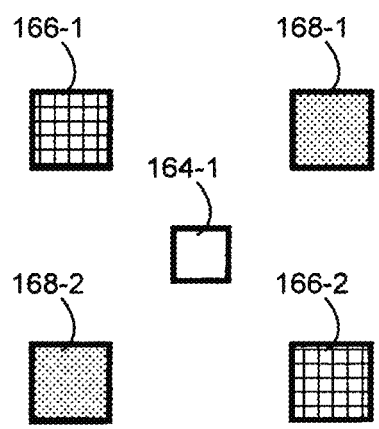

FIG. 1K and 1L are schematic diagrams illustrating light elements in accordance with some embodiments.

FIG. 1K illustrates light elements (e.g., subpixels), including light elements 164 of a first type (e.g., light elements configured to generate green light, such as light elements 164-1, 164-2, 164-3, and 164-4), light elements 166 of a second type (e.g., light elements configured to generate blue light, such as light elements 166-1, 166-2, 166-3, and 166-4), and light elements 168 of a third type (e.g., light elements configured to generate red light, such as light elements 168-1, 168-2, 168-3, and 168-4). In some embodiments, light elements are part of light emission device array 110 (e.g., light elements 164, 166, and 168 are part of liquid crystal display pixels).

FIG. 1L illustrates that five light elements are used in some embodiments. In some embodiments, array 160-1 includes only five light elements. In some embodiments, light elements other than the first light elements are deactivated (e.g., turned off) while a position of lens 130-1 relative to eye 140-1 is determined and/or lens 130-1 is aligned with eye 140-1.

Figure 1M:
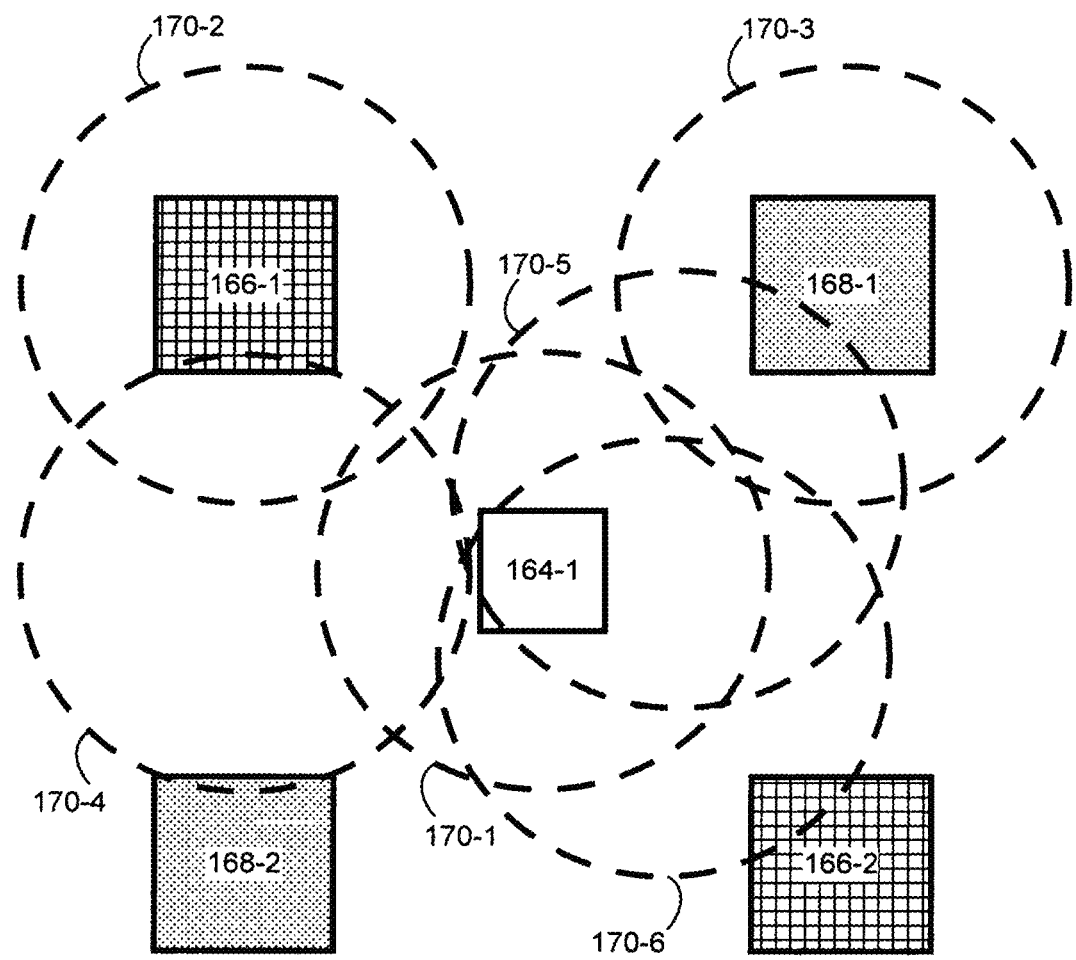
FIG. 1M is a schematic diagram illustrating portions of light transmitted through an entrance pupil of an eye in accordance with some embodiments.

FIG. 1M is a schematic diagram illustrating portions of light transmitted through an entrance pupil of an eye in accordance with some embodiments.

Five light elements shown in FIG. 1L project (using lens 162-1 and first set 130-1 of one or more lenses) on an entrance pupil plane images of the five light elements 164-1, 166-1, 166-2, 168-1, and 168-2.

When an entrance pupil of an eye (e.g., eye 140-1) is at position 170-1, only light from light element 164-1 is transmitted through the entrance pupil (e.g., light from light elements 166-1, 168-1, 168-2, and 166-2 are not transmitted through the entrance pupil). When the entrance pupil is at position 170-2, only light from light element 166-1 is transmitted through the entrance pupil (e.g., light from light elements 168-1, 164-1, 168-2, and 166-2 are not transmitted through the entrance pupil). When the entrance pupil is at position 110-3, only light from light element 168-1 is transmitted through the entrance pupil (e.g., light from light elements 166-1, 164-1, 168-2, and 166-2 are not transmitted through the entrance pupil).

When the entrance pupil is at position 170-4, a portion of light from light element 166-1 and a portion of light from light element 168-2 are transmitted through the entrance pupil. When the entrance pupil is at location 170-5, a portion of light from light element 164-1 and a portion of light from light element 168-1 are transmitted through the entrance pupil. When the entrance pupil is at location 170-6, a portion of light from light element 164-1 and a portion of light from light element 166-2 are transmitted through the entrance pupil.

Figure 1N:
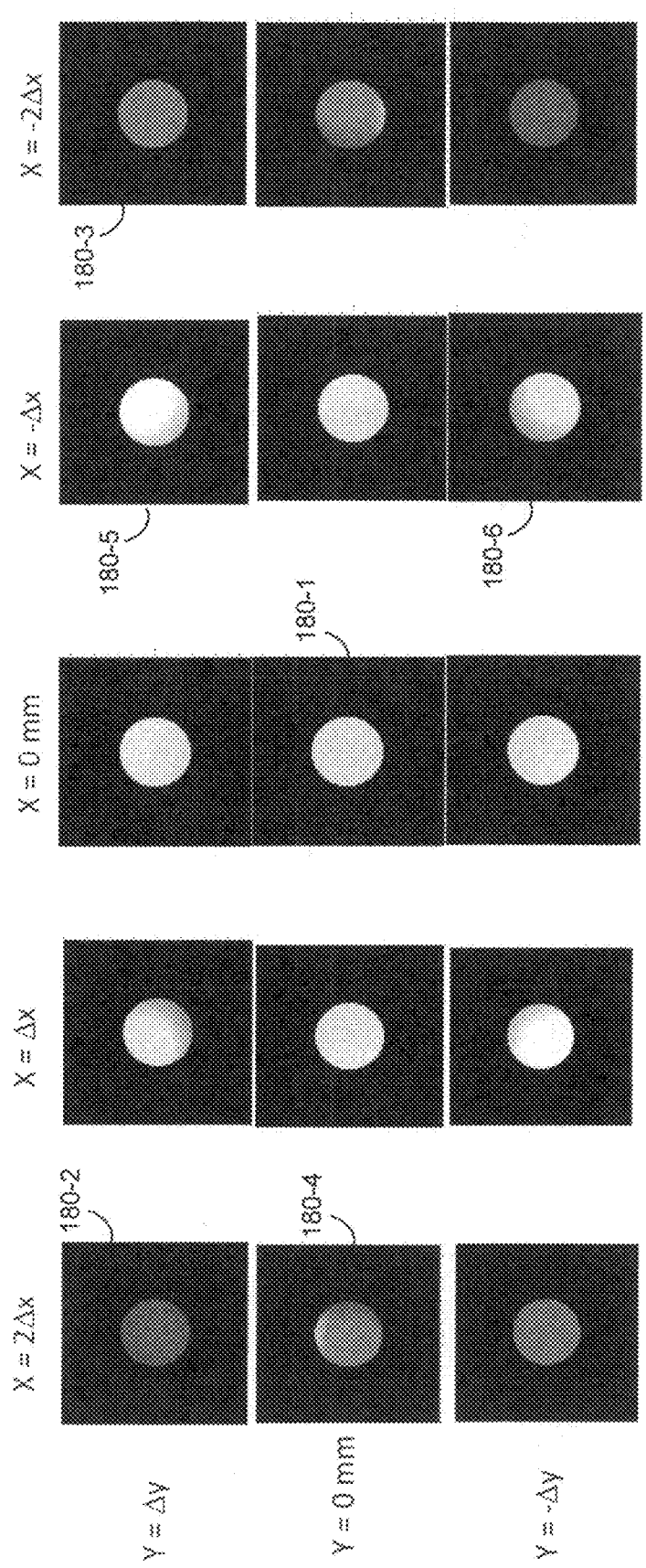
FIG. 1N illustrates colors of received light based on a position of an entrance pupil of an eye in accordance with some embodiments.
Figure 10:
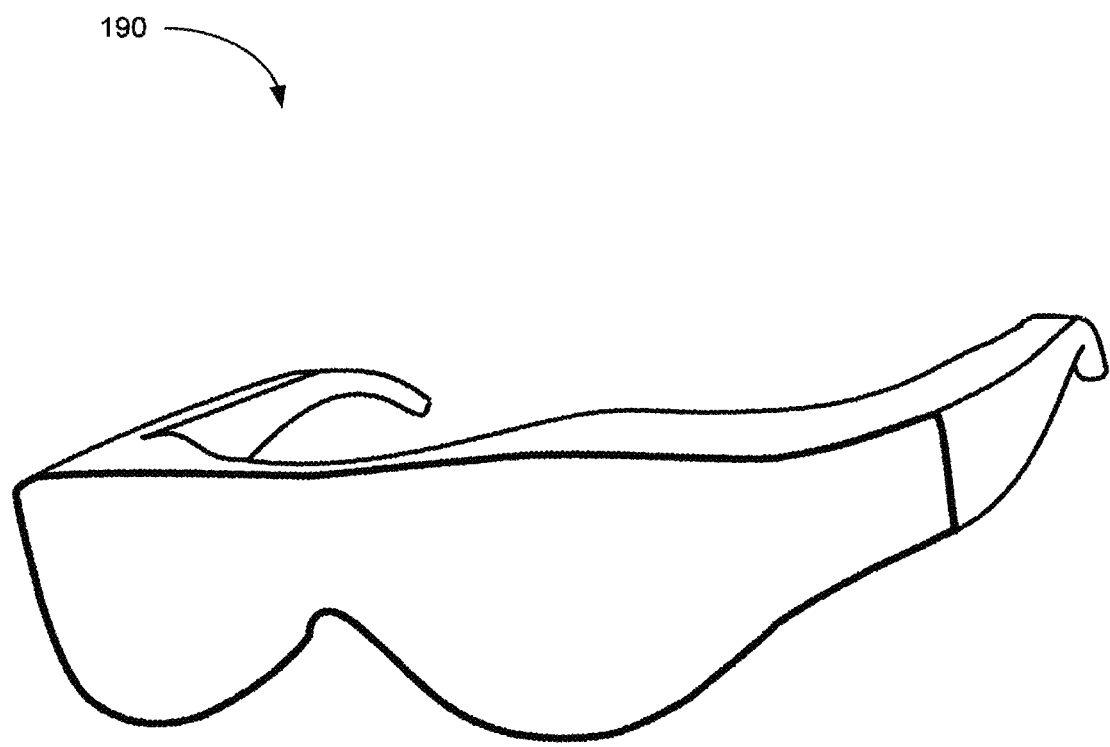

FIG. 1N illustrates colors of received light based on a position of an entrance pupil of an eye in accordance with some embodiments. In FIG. 1N, a position of the entrance pupil is represented by an x-coordinate and a y-coordinate. In some cases, $\Delta x$ equals 1 mm, and $\Delta y$ equals 1 mm. In some cases, $\Delta x$ equals 0.5 mm, and $\Delta y$ equals 1 mm.

Image 180-1 shows a color of light received while the entrance pupil is at position 170-1 (FIG. 1M). Because only light from light element 164-1 (e.g., green light) is transmitted through the entrance pupil, the received light has a green color.

Image 180-2 shows a color of light received while the entrance pupil is at position 170-2 (FIG. 1M). Because only light from light element 166-1 (e.g., blue light) is transmitted through the entrance pupil, the received light has a blue color.

Image 180-3 shows a color of light received while the entrance pupil is at position 170-3 (FIG. 1M). Because only light from light element 168-1 (e.g., red light) is transmitted through the entrance pupil, the received light has a red color.

Image 180-4 shows a color of light received while the entrance pupil is at position 170-4 (FIG. 1M). Because a portion of light from light element 166-1 (e.g., blue light) and a portion of light from light element 168-2 (red light) are transmitted through the entrance pupil, the received light has a magenta color.

Image 180-5 shows a color of light received while the entrance pupil is at position 170-5 (FIG. 1M). Because a portion of light from light element 168-1 (e.g., red light) and a portion of light from light element 164-1 (e.g., green light) arc transmitted through the entrance pupil, the received light has a yellow color.

Image 180-6 shows a color of light received while the entrance pupil is at position 170-6 (FIG. 1M). Because a portion of light from light element 168-1 (e.g., blue light) and a portion of light from light element 164-1 (e.g., green light) are transmitted through the entrance pupil, the received light has a cyan color.

Thus, the color of the received light indicates whether a lens (e.g., first set 130-1 of one or more lenses) is aligned with an eye or not. For example, in FIG. 1N, a green light indicates that the lens is aligned with the eye, and any color other than the green light indicates that the lens is not aligned with the eye. In some cases, the color of the received light also indicates a direction and/or a distance of an offset between the lens and the eye. For example, a blue color in the received light indicates that the lens is offset diagonally upper-left or lower-right from the eye, a red color in the received light indicates that the lens is offset diagonally upper-right or lower-left from the eye, a magenta color in the received light indicates that the lens is offset horizontally from the eye (e.g., by 2Δx).

FIG. 1O illustrates display device 190 in accordance with some embodiments. In some embodiments, display device 190 is configured to be worn on a head of a user (e.g., by having the form of spectacles or eyeglasses, as shown in FIG. 1O) or to be included as part of a helmet that is to be worn by the user. When display device 190 is configured to be worn on a head of a user or to be included as part of a helmet, display device 190 is called a head-mounted display. Alternatively, display device 190 is configured for placement in proximity of an eye or eyes of the user at a fixed location, without being head-mounted (e.g., display device 190 is mounted in a vehicle, such as a car or an airplane, for placement in front of an eye or eyes of the user).

In some embodiments, display device 190 includes one or more components described below with respect to FIG. 2. In some embodiments, display device 190 includes additional components not shown in FIG. 2.

Figure 2:
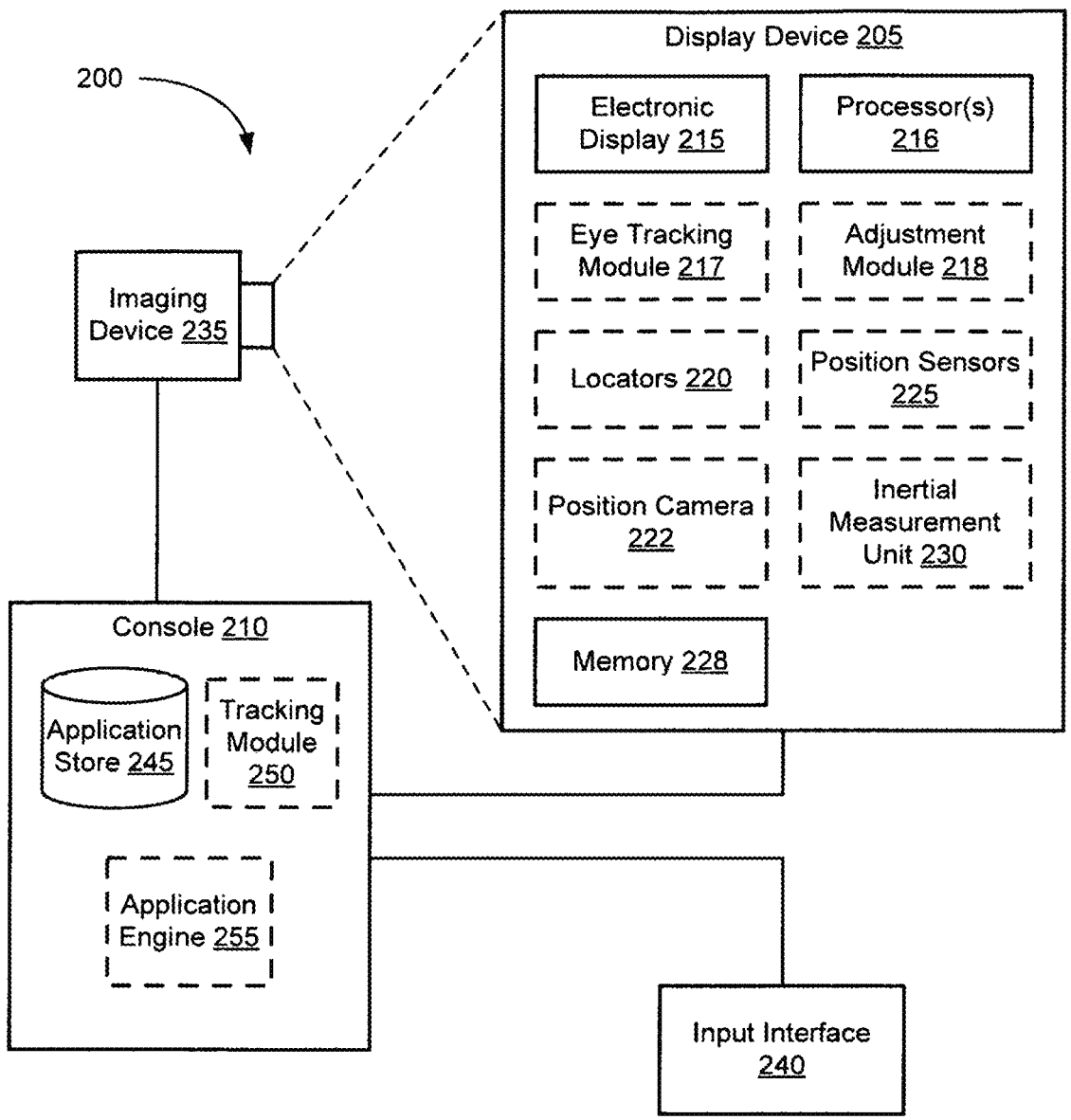
FIG. 2 is a block diagram of a system including a display device in accordance with some embodiments.

FIG. 2 is a block diagram of system 200 in accordance with some embodiments. The system 200 shown in FIG. 2 includes display device 205 (which corresponds to display device 190 shown in FIG. 1O), imaging device 235, and input interface 240 that are each coupled to console 210. While FIG. 2 shows an example of system 200 including one display device 205, imaging device 235, and input interface 240, in other embodiments, any number of these components may be included in system 200. For example, there may be multiple display devices 205 each having associated input interface 240 and being monitored by one or more imaging devices 235, with each display device 205, input interface 240, and imaging devices 235 communicating with console 210. In alternative configurations, different and/or additional components may be included in system 200. For example, in some embodiments, console 210 is connected via a network (e.g., the Internet) to system 200 or is self-contained as part of display device 205 (e.g., physically located inside display device 205). In some embodiments, display device 205 is used to create mixed reality by adding in a view of the real surroundings. Thus, display device 205 and system 200 described here can deliver virtual reality, mixed reality, and augmented reality.

In some embodiments, as shown in FIG. 1O, display device 205 is a head-mounted display that presents media to a user. Examples of media presented by display device 205 include one or more images, video, audio, or some combination thereof. In some embodiments, audio is presented via an external device (e.g., speakers and/or headphones) that receives audio information from display device 205, console 210, or both, and presents audio data based on the audio information. In some embodiments, display device 205 immerses a user in a virtual environment.

In some embodiments, display device 205 also acts as an augmented reality (AR) headset. In these embodiments, display device 205 augments views of a physical, real-world environment with computer-generated elements (e.g., images, video, sound, etc.). Moreover, in some embodiments, display device 205 is able to cycle between different types of operation. Thus, display device 205 operate as a virtual reality (VR) device, an AR device, as glasses or some combination thereof (e.g., glasses with no optical correction, glasses optically corrected for the user, sunglasses, or some combination thereof) based on instructions from application engine 255.

Display device 205 includes electronic display 215, one or more processors 216, eye tracking module 217, adjustment module 218, one or more locators 220, one or more position sensors 225, one or more position cameras 222, memory 228, inertial measurement unit (IMU) 230, or a subset or superset thereof (e.g., display device 205 with electronic display 215, one or more processors 216, and memory 228, without any other listed components). Some embodiments of display device 205 have different modules than those described here. Similarly, the functions can be distributed among the modules in a different manner than is described here.

One or more processors 216 (e.g., processing units or cores) execute instructions stored in memory 228. Memory 228 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 228, or alternately the non-volatile memory device(s) within memory 228, includes a non-transitory computer readable storage medium. In some embodiments, memory 228 or the computer readable storage medium of memory 228 stores programs, modules and data structures, and/or instructions for displaying one or more images on electronic display 215.

Electronic display 215 displays images to the user in accordance with data received from console 210 and/or processor(s) 216. In various embodiments, electronic display 215 may comprise a single adjustable electronic display element or multiple adjustable electronic displays elements (e.g., a display for each eye of a user).

In some embodiments, the display element includes one or more light emission devices and a corresponding array of emission intensity array. An emission intensity array is an array of electro-optic pixels, opto-electronic pixels, some other array of devices that dynamically adjust the amount of light transmitted by each device, or some combination thereof. These pixels are placed behind one or more lenses. In some embodiments, the emission intensity array is an array of liquid crystal based pixels in an LCD (a Liquid Crystal Display). Examples of the light emission devices include: an organic light emitting diode, an active-matrix organic light-emitting diode, a light emitting diode, some type of device capable of being placed in a flexible display, or some combination thereof. The light emission devices include devices that are capable of generating visible light (e.g., red, green, blue, etc.) used for image generation. The emission intensity array is configured to selectively attenuate individual light emission devices, groups of light emission devices, or some combination thereof Alternatively, when the light emission devices are configured to selectively attenuate individual emission devices and/or groups of light emission devices, the display element includes an array of such light emission devices without a separate emission intensity array.

One or more lenses direct light from the arrays of light emission devices (optionally through the emission intensity arrays) to locations within each eyebox and ultimately to the back of the user's retina(s). An eyebox is a region that is occupied by an eye of a user located proximity to display device 205 (e.g., a user wearing display device 205) for viewing images from display device 205. In some cases, the eyebox is represented as a 10 mm×10 mm square. In some embodiments, the one or more lenses include one or more coatings, such as anti-reflective coatings.

In some embodiments, the display element includes an infrared (IR) detector array that detects IR light that is retro-reflected from the retinas of a viewing user, from the surface of the corneas, lenses of the eyes, or some combination thereof. The IR detector array includes an IR sensor or a plurality of IR sensors that each correspond to a different position of a pupil of the viewing user's eye. In alternate embodiments, other eye tracking systems may also be employed.

Eye tracking module 217 determines locations of each pupil of a user's eyes. In some embodiments, eye tracking module 217 instructs electronic display 215 to illuminate the eyebox with IR light (e.g., via IR emission devices in the display element).

A portion of the emitted IR light will pass through the viewing user's pupil and be retro-reflected from the retina toward the IR detector array, which is used for determining the location of the pupil. Alternatively, the reflection off of the surfaces of the eye is used to also determine location of the pupil. The IR detector array scans for retro-reflection and identifies which IR emission devices are active when retro-reflection is detected. Eye tracking module 217 may use a tracking lookup table and the identified IR emission devices to determine the pupil locations for each cyc. The tracking lookup table maps received signals on the IR detector array to locations (corresponding to pupil locations) in each eyebox. In some embodiments, the tracking lookup table is generated via a calibration procedure (e.g., user looks at various known reference points in an image and eye tracking module 217 maps the locations of the user's pupil while looking at the reference points to corresponding signals received on the IR tracking array). As mentioned above, in some embodiments, system 200 may use other eye tracking systems than the embedded IR one described above.

Adjustment module 218 generates an image frame based on the determined locations of the pupils. In some embodiments, this sends a discrete image to the display that will tile subimages together thus a coherent stitched image will appear on the back of the retina. Adjustment module 218 adjusts an output (i.e. the generated image frame) of electronic display 215 based on the detected locations of the pupils. Adjustment module 218 instructs portions of electronic display 215 to pass image light to the determined locations of the pupils. In some embodiments, adjustment module 218 also instructs the electronic display to not pass image light to positions other than the determined locations of the pupils. Adjustment module 218 may, for example, block and/or stop light emission devices whose image light falls outside of the determined pupil locations, allow other light emission devices to emit image light that falls within the determined pupil locations, translate and/or rotate one or more display elements, dynamically adjust curvature and/or refractive power of one or more active lenses in the lens (e.g., microlens) arrays, or some combination thereof Optional locators 220 are objects located in specific positions on display device 205 relative to one another and relative to a specific reference point on display device 205. A locator 220 may be a light emitting diode (LED), a corner cube reflector, a reflective marker, a type of light source that contrasts with an environment in which display device 205 operates, or some combination thereof In embodiments where locators 220 are active (i.e., an LED or other type of light emitting device), locators 220 may emit light in the visible band (e.g., about 400 nm to 750 nm), in the infrared band (e.g., about 750 nm to 1 mm), in the ultraviolet band (about 100 nm to 400 nm), some other portion of the electromagnetic spectrum, or some combination thereof.

In some embodiments, locators 220 are located beneath an outer surface of display device 205, which is transparent to the wavelengths of light emitted or reflected by locators 220 or is thin enough to not substantially attenuate the wavelengths of light emitted or reflected by locators 220. Additionally, in some embodiments, the outer surface or other portions of display device 205 are opaque in the visible band of wavelengths of light. Thus, locators 220 may emit light in the IR band under an outer surface that is transparent in the IR band but opaque in the visible band.

IMU 230 is an electronic device that generates calibration data based on measurement signals received from one or more position sensors 225. Position sensor 225 generates one or more measurement signals in response to motion of display device 205. Examples of position sensors 225 include: one or more accelerometers, one or more gyroscopes, one or more magnetometers, another suitable type of sensor that detects motion, a type of sensor used for error correction of IMU 230, or some combination thereof. Position sensors 225 may be located external to IMU 230, internal to IMU 230, or some combination thereof.

Based on the one or more measurement signals from one or more position sensors 225, IMU 230 generates first calibration data indicating an estimated position of display device 205 relative to an initial position of display device 205. For example, position sensors 225 include multiple accelerometers to measure translational motion (forward/back, up/down, left/right) and multiple gyroscopes to measure rotational motion (e.g., pitch, yaw, roll). In some embodiments, IMU 230 rapidly samples the measurement signals and calculates the estimated position of display device 205 from the sampled data. For example, IMU 230 integrates the measurement signals received from the accelerometers over time to estimate a velocity vector and integrates the velocity vector over time to determine an estimated position of a reference point on display device 205. Alternatively, IMU 230 provides the sampled measurement signals to console 210, which determines the first calibration data. The reference point is a point that may be used to describe the position of display device 205. While the reference point may generally be defined as a point in space; however, in practice the reference point is defined as a point within display device 205 (e.g., a center of IMU 230).

In some embodiments, TMTJ 230 receives one or more calibration parameters from console 210. As further discussed below, the one or more calibration parameters are used to maintain tracking of display device 205. Based on a received calibration parameter, IMU 230 may adjust one or more IMU parameters (e.g., sample rate). In some embodiments, certain calibration parameters cause IMU 230 to update an initial position of the reference point so it corresponds to a next calibrated position of the reference point. Updating the initial position of the reference point as the next calibrated position of the reference point helps reduce accumulated error associated with the determined estimated position. The accumulated error, also referred to as drift error, causes the estimated position of the reference point to "drift" away from the actual position of the reference point over time.

Imaging device 235 generates calibration data in accordance with calibration parameters received from console 210. Calibration data includes one or more images showing observed positions of locators 220 that are detectable by imaging device 235. In some embodiments, imaging device 235 includes one or more still cameras, one or more video cameras, any other device capable of capturing images including one or more locators 220, or some combination thereof. Additionally, imaging device 235 may include one or more filters (e.g., used to increase signal to noise ratio). Imaging device 235 is configured to optionally detect light emitted or reflected from locators 220 in a field of view of imaging device 235. In embodiments where locators 220 include passive elements (e.g., a retroreflector), imaging device 235 may include a light source that illuminates some or all of locators 220, which retro-reflect the light towards the light source in imaging device 235. Second calibration data is communicated from imaging device 235 to console 210, and imaging device 235 receives one or more calibration parameters from console 210 to adjust one or more imaging parameters (e.g., focal length, focus, frame rate, ISO, sensor temperature, shutter speed, aperture, etc.).

Input interface 240 is a device that allows a user to send action requests to console 210. An action request is a request to perform a particular action. For example, an action request may be to start or end an application or to perform a particular action within the application. Input interface 240 may include one or more input devices. Example input devices include: a keyboard, a mouse, a game controller, data from brain signals, data from other parts of the human body, or any other suitable device for receiving action requests and communicating the received action requests to console 210. An action request received by input interface 240 is communicated to console 210, which performs an action corresponding to the action request. In some embodiments, input interface 240 may provide haptic feedback to the user in accordance with instructions received from console 210. For example, haptic feedback is provided when an action request is received, or console 210 communicates instructions to input interface 240 causing input interface 240 to generate haptic feedback when console 210 performs an action.

Console 210 provides media to display device 205 for presentation to the user in accordance with information received from one or more of: imaging device 235, display device 205, and input interface 240. In the example shown in FIG. 2, console 210 includes application store 245, tracking module 250, and application engine 255. Some embodiments of console 210 have different modules than those described in conjunction with FIG. 2. Similarly, the functions further described below may be distributed among components of console 210 in a different manner than is described here.

When application store 245 is included in console 210, application store 245 stores one or more applications for execution by console 210. An application is a group of instructions, that when executed by a processor, is used for generating content for presentation to the user. Content generated by the processor based on an application may be in response to inputs received from the user via movement of display device 205 or input interface 240. Examples of applications include: gaming applications, conferencing applications, video playback application, or other suitable applications.

When tracking module 250 is included in console 210, tracking module 250 calibrates system 200 using one or more calibration parameters and may adjust one or more calibration parameters to reduce error in determination of the position of display device 205. For example, tracking module 250 adjusts the focus of imaging device 235 to obtain a more accurate position for observed locators on display device 205. Moreover, calibration performed by tracking module 250 also accounts for information received from IMU 230. Additionally, if tracking of display device 205 is lost (e.g., imaging device 235 loses line of sight of at least a threshold number of locators 220), tracking module 250 re-calibrates some or all of system 200.

In some embodiments, tracking module 250 tracks movements of display device 205 using second calibration data from imaging device 235. For example, tracking module 250 determines positions of a reference point of display device 205 using observed locators from the second calibration data and a model of display device 205. In some embodiments, tracking module 250 also determines positions of a reference point of display device 205 using position information from the first calibration data. Additionally, in some embodiments, tracking module 250 may use portions of the first calibration data, the second calibration data, or some combination thereof, to predict a future location of display device 205. Tracking module 250 provides the estimated or predicted future position of display device 205 to application engine 255.

Application engine 255 executes applications within system 200 and receives position information, acceleration information, velocity information, predicted future positions, or some combination thereof of display device 205 from tracking module 250. Based on the received information, application engine 255 determines content to provide to display device 205 for presentation to the user. For example, if the received information indicates that the user has looked to the left, application engine 255 generates content for display device 205 that mirrors the user's movement in a virtual environment. Additionally, application engine 255 performs an action within an application executing on console 210 in response to an action request received from input interface 240 and provides feedback to the user that the action was performed. The provided feedback may be visual or audible feedback via display device 205 or haptic feedback via input interface 240.

In light of these principles, we now turn to certain embodiments.

In accordance with some embodiments, a device includes a first light source device (e.g., light source device 122-1 in FIG. 1B) configured to transmit a first light (e.g., first light 132-1) in a first direction and a second light (e.g., second light 132-2) in a second direction that is distinct from the first direction. The device also includes a first set of one or more lenses (e.g., lens 130-1 in FIG. 1B) configured for directing the first light and the second light from the first light source device toward a first eye of a user. The first light is spatially offset from the second light (e.g., first light 132-1 is spatially offset from second light 134-1 as shown in FIG. 1B). One or more of the first light and the second light provide a cue for adjusting a location (e.g., a lateral location) of the first set of one or more lenses.

In some embodiments, the first light indicates that an eye receiving the first light is offset from a center of the first set of one or more lenses (e.g., as shown in FIG. 1D, when eye 140-1 receives first light 132-1, this indicates that eye 140-1 is offset from a lateral position of a center of lens 130-1). The second light indicates that an eye receiving the second light is aligned with the center of the first set of one or more lenses (e.g., as shown in FIG. 1B, when eye 140-1 receives second light 134-1, this indicates that eye 140-1 is aligned with the lateral position of the center of lens 130-1).

In some embodiments, the first light directed to the first eye is parallel to the second light directed to the first eye (e.g., in FIG. 1B, first light 132-1 is parallel to second light 134-1 after passing through lens 130-1).

In some embodiments, the first light source device is further configured to transmit a third light in a third direction that is distinct from the first direction and the second direction; and the first set of one or more lenses is further configured for directing the third light toward the first eye (e.g., in FIG. 1B, third light 136-1). The third light is spatially offset from the first light and the second light.

In some embodiments, the first light has a first color (e.g., red), and the second light has a second color (e.g., green) that is distinct from the first color. The first light source device includes a light emitting component configured to provide a broadband light that includes the first light of the first color and the second light of the second color; and an optical grating (e.g., optical grating 148 in FIG. 1H) configured to disperse the broadband light from the light emitting component, including directing the first light of the first color in the first direction and the second light of the second color in the second direction.

In some embodiments, the first light has a first color (e.g., red), and the second light has a second color (e.g., green) that is distinct from the first color. the first light source device includes a light emitting component configured to provide a broadband light that includes the first light of the first color and the second light of the second color; and a plurality of dichroic mirrors (e.g., set 152 of dichroic mirrors in FIG. 1I), including a first dichroic mirror and a second dichroic mirror. The first dichroic mirror is configured to reflect the first light of the first color in the first direction and the second dichroic mirror is configured to reflect the second light of the second color in the second direction.

In some embodiments, the first light source device includes a first light emitting component (e.g., first light emitting component 142-1 in FIG. 1F) configured to provide the first light and a second light emitting component (e.g., second light emitting component 142-2 in FIG. 1F) configured to provide the second light.

In some embodiments, the first light has a first color (e.g., red), and the second light has a second color (e.g., green) that is distinct from the first color.

In some embodiments, the first light has a first time-dependent intensity pattern (e.g., a first pulsing frequency, a first duty cycle, a first interval, etc.) and the second light has a second time-dependent intensity pattern (e.g., a second pulsing frequency, a second duty cycle, a second interval, etc.). In some embodiments, the second time-dependent intensity pattern is distinct from the first time-dependent intensity pattern.

In some embodiments, the first light emitting component is configured to provide the first light in multiple directions, and the second light emitting component is configured to provide the second light in multiple directions (e.g., FIG. 1F). The first light source device also includes one or more lenses (e.g., lens 144 in FIG. 1F). The first light emitting component and the second light emitting component are positioned (e.g., on a focal plane of the one or more lenses) with a lateral offset so that the first light provided by the first light emitting component is directed to the first direction and the second light provided by the second light emitting component is directed to the second direction.

In some embodiments, the first light source device also includes a barrier having an opening (e.g., barrier 146 with a pinhole or a slit, as shown in FIG. 1G) configured to transmit the first light from the first light emitting component in the first direction and the second light from the second light emitting component in the second direction. In some embodiments, the first light emitting component is configured to provide the first light in multiple directions, and the second light emitting component is configured to provide the second light in multiple directions.

In some embodiments, the device includes a second light source device (e.g., second light source device 122-1 in FIG. 1B) configured to transmit a fourth light (e.g., fourth light 132-2 in FIG. 1B) in a fourth direction and a fifth light (e.g., fifth light 134-2 in FIG. 1B) distinct from the fourth light in a fifth direction that is distinct from the fourth direction. The second light source device is distinct from the first light source device. The device also includes a second set of one or more lenses (e.g., lens 130-2 in FIG. 1B) configured for directing the fourth light and the fifth light from the second light source device toward a second eye of the user. The fourth light is spatially offset from the fifth light. One or more of the fourth light and the fifth light provide a cue for adjusting a location (e.g., a lateral location) of the second set of one or more lenses.

In some embodiments, the second light source device is further configured to transmit a sixth light (e.g., sixth light 136-2 in FIG. 1B) in a sixth direction that is distinct from the fourth direction and the fifth direction. The second set of one or more lenses is further configured for directing the sixth light toward the second eye. The sixth light is spatially offset from the fourth light and the fifth light.

In some embodiments, the device also includes one or more display screens (e.g., display screens 110-1 and/or 110-2) configured to project one or more images through the first set of one or more lenses.

In some embodiments, the device is a head-mounted display device (e.g., FIG. 1O).

In accordance with some embodiments, a method includes transmitting a first light (e.g., first light 132-1 in FIG. 1B) in a first direction and a second light (e.g., second light 134-1 in FIG. 1B) that is distinct from the first light in a second direction that is distinct from the first direction; and transmitting the first light and the second light through a first set of one or more lenses and directing the first light and the second light toward a first eye of a user (e.g., FIG. 1B). The first light is spatially offset from the second light and one or more of the first light and the second light provide a cue for adjusting a location of the first set of one or more lenses.

In some embodiments, the method also includes, in conjunction with transmitting the first light and the second light through the first set of one or more lenses (e.g., concurrently with transmitting the first light and the second light through the first set of one or more lenses), transmitting a third light that is distinct and spatially offset from the first light and the second light.

In some embodiments, the method also includes transmitting a fourth light (e.g., fourth light 132-2 in FIG. 1B) in a fourth direction and a fifth light (e.g., fifth light 134-2 in FIG. 1B) that is distinct form the fourth light in a fifth direction that is distinct from the fourth direction; and transmitting the fourth light and the fifth light through a second set of one or more lenses that is distinct from the first set of one or more lenses and directing the fourth light and the fifth light toward a second eye of the user. The fourth light is spatially offset from the fifth light and one or more of the fourth light and the fifth light provide a cue for adjusting a location of the second set of one or more lenses.

In some embodiments, the method also includes, in conjunction with transmitting the first light and the second light through the first set of one or more lenses, transmitting a reference light from one or more display screens through the first set of one or more lenses (e.g., reference light 138). In some embodiments, the reference light has a color and/or a time-dependent intensity pattern of the second light. Thus, the reference light can assist with a determination whether the second light is received by an eye. For example, a color of the reference light and a color of light from a light source device are compared to determine whether the color of the light from the light source device matches the color of the reference light. If the color of the light from the light source device matches the color of the reference light, the lens is aligned with the eye. If the color of the light from the light source device does not match the color of the reference light, the lens is not aligned with the eye. In another example, a pulsing frequency of the reference light and a pulsing frequency of light from a light source device are compared to determine whether the pulsing frequency of the light from the light source device matches the pulsing frequency of the reference light. If the pulsing frequency of the light from the light source device matches the pulsing frequency of the reference light, the lens is aligned with the eye. If the pulsing frequency of the light from the light source device does not match the pulsing frequency of the reference light, the lens is not aligned with the eye.

In accordance with some embodiments, a method includes receiving a portion of a bundle of light that includes a first light and a second light that is distinct from the first light and laterally offset from the first light (e.g., FIG. 1B). The method also includes, in accordance with a determination that the received portion of the bundle of light corresponds to the first light, moving the first set of one or more lenses. For example, when the received portion of the bundle of light has a first color (e.g., in FIG. 1D, the received portion of the bundle of light has a red color, which indicates that lens 130-1 needs to be moved toward a left side to align with eye 140-1), the first set of one or more lenses is moved toward the left side.

In some embodiments, the method further includes continuing to monitor the color of a light received by an eye and adjust a lateral position of the lens (or continuing to monitor the color of a light received by each eye and adjust lateral positions of the first lens and the second lens) until the first lens is accurately positioned (or both the first lens and the second lens are accurately positioned). In some embodiments, an accurate positioning of a lens is indicated by whether a particular light (e.g., having a particular color, such as green, and/or having a particular time-dependent intensity pattern, such as a pulsing frequency, a duty cycle, and/or an interval) is delivered toward a pupil of an eye.

In accordance with some embodiments, a method includes transmitting a first light in a first direction, and transmitting the first light through a first set of one or more lenses and directing the first light toward a first eye of a user. The first light is spatially restricted. The first light provides a cue for adjusting a location of the first set of one or more lenses.

In accordance with some embodiments, a method includes receiving at least a portion of a bundle of a first light that is spatially restricted. The method also includes, in accordance with a determination that the at least a portion of a bundle of the first light is received, moving the first set of one or more lenses (e.g., based on an intensity of the received portion of the bundle of the first light so that a center of the bundle of the first light is received by a first eye of a user). Alternatively, the method includes, in accordance with a determination that no portion of the bundle of the first light is received, moving the first set of one or more lenses (because the first set of one or more lenses is not aligned with the first eye of the user).

In accordance with some embodiments, a head-mounted display device includes a first light source device (e.g., array 160-1 of light elements, FIG. 1J) that includes a first light element (e.g., light element 164-1, FIG. 1L) configured to transmit a first light having a first color (e.g., green light); a second light element (e.g., light element 166-1, FIG. 1L) configured to transmit a second light having a second color (e.g., blue light) that is distinct from the first color, the second light element being distinct and separate from the first light element; and a first lens (e.g., lens 162-1) configured for directing the first light from the first light element in a first direction and directing the second light from the second light element in a second direction that is distinct from the first direction. The device also includes a first set of one or more lenses (e.g., lens 130-1) configured for directing the first light and the second light from the first lens toward a first eye of a user.

In some embodiments, the first light is spatially offset from the second light upon reaching the first eye of the user (e.g., as shown in FIG. 1J, the green light is laterally offset from the blue light).

In some embodiments, the device includes one or more electronic displays that include an array of light elements, including a reference light element configured to transmit a reference light having the first color based on information stored in the device. In some embodiments, the reference light is provided during alignment of the first set of one or more lenses (e.g., while the device is worn by a user) to facilitate the alignment of the first set of one or more lenses with the first eye of the user. In some cases, because light elements (e.g., subpixels) and the first lens (e.g., a microlens) are small, it is difficult to precisely align the light elements and the first lens. Thus, instead of align the light elements and the first lens perfectly, a color of light received by a camera, that is in alignment with the first set of one or more lenses, is recorded and selected as a color of the reference light (typically during manufacturing of the device). For example, based on information indicating that the light received by the camera is a green light, a reference light element configured to transmit a green light is selected. In another example, based on information indicating that the light received by the camera is a red light, a reference light element configured to transmit a red light is selected. The one or more electronic displays are configured to display one or more images and the first set of one or more lenses are configured to direct light from the one or more electronic displays toward the first eye of the user.

In some embodiments, the first light source device also includes: a third light element (e.g., light element 168-1, FIG. 1L) configured to transmit a third light having a third color (e.g., red light) that is distinct from the first color and the second color, the third light element being distinct and separate from the first light element and the second light element; the first lens is configured for directing the third light from the third light element in a third direction that is distinct from the first direction and the second direction; and the first set of one or more lenses are configured for directing the third light from the first lens toward the first eye of the user.

In some embodiments, the first light source device also includes: a fourth light element (e.g., light element 166-2, FIG. 1L) configured to transmit a fourth light having the second color (e.g., blue light), the fourth light element being distinct and separate from the first light element, the second light element, and the third light element; and a fifth light element (e.g., light element 168-2, FIG. 1L) configured to transmit a fifth light having the third color (e.g., red light), the fifth light element being distinct and separate from the first light element, the second light element, the third light element, and the fourth light element; the first lens is configured for directing the fourth light from the fourth light element in a fourth direction that is distinct from the first direction, the second direction, and the third direction and directing the fifth light from the fifth light element in a fifth direction that is distinct from the first direction, the second direction, the third direction, and the fourth direction; and the first set of one or more lenses are configured for directing the fourth light and the fifth light from the first lens toward the first eye of the user.

In some embodiments, the first lens defines a first optical axis; and the first light element is located on the first optical axis.

In some embodiments, the first light source device also includes: a fourth light element (e.g., light element 166-2, FIG. 1L) configured to transmit a fourth light having the second color, the fourth light element being distinct and separate from the first light element and the second light element; the first lens is configured for directing the fourth light from the fourth light element in a fourth direction that is distinct from the first direction and the second direction; and the first set of one or more lenses are configured for directing the fourth light from the first lens toward the first eye of the user. For example, the first light source device includes the first light element, the second light element, and the fourth light element without any other light element (e.g., the first light source device includes light elements 164-1, 166-1, and 166-2 without light element 168-1 or 168-2).

In some embodiments, the first light source device, the first lens, and the first set of one or more lenses are configured so that the first light and the second light are separated by at least 2 mm on an entrance pupil of the first eye. In some embodiments, the first light source device, the first lens, and the first set of one or more lenses are configured so that the first light and the second light are separated by at least 1 mm on an entrance pupil of the first eye. In some embodiments, the first light source device, the first lens, and the first set of one or more lenses are configured so that the first light and the second light are separated by at least 3 mm on an entrance pupil of the first eye.

In some embodiments, the first light source device, the first lens, and the first set of one or more lenses are configured so that the first light and the second light are separated by no more than a diameter of an entrance pupil of the first eye. In some embodiments, the first light source device, the first lens, and the first set of one or more lenses are configured so that the first light and the second light are separated by no more than 5 mm. In some embodiments, the first light source device, the first lens, and the first set of one or more lenses are configured so that the first light and the second light are separated by no more than 4 mm. In some embodiments, the first light source device, the first lens, and the first set of one or more lenses are configured so that the first light and the second light are separated by no more than 3 mm. This facilitates that the entrance pupil continues to receive guiding light in areas adjacent to the spots illuminated by the first light source device. Because, in some cases, the absence of light makes the aligning operation more challenging for the users, continuing to provide guiding light to the entrance pupil facilitates the aligning operations.

In some embodiments, the device also includes a second light source device that includes: a sixth light element configured to transmit a sixth light having the first color; a seventh light element configured to transmit a seventh light having the second color, the seventh light element being distinct and separate from the sixth light element; and a second lens configured for directing the sixth light from the sixth light element in a sixth direction and directing the seventh light from the seventh light element in a seventh direction that is distinct from the sixth direction. The device further includes a second set of one or more lenses configured for directing the sixth light and the seventh light from the second lens toward a second eye of the user that is distinct from the first eye of the user. For example, the device includes a light source device and a respective set of one or more lenses for each eye. The structures and operations of the second light source device and the second set of one or more lenses are similar to the structures and operations of the first light source device and the first set of one or more lenses. For brevity, the structures and operations of the second light source device and the second set of one or more lenses are omitted herein.

In some embodiments, the device also includes mounts configured for holding the first set of one or more lenses and the second set of one or more lenses and adjusting a distance between the first set of one or more lenses and the second set of one or more lenses. In some embodiments, the mounts include one or more rails configured to adjust a representative distance between the first set of one or more lenses and the second set of one or more lenses (e.g., a distance between a particular lens of the first set of one or more lenses and a corresponding lens of the second set of one or more lenses). In some embodiments, the mounts include one or more actuators configured to adjust the representative distance between the first set of one or more lenses. In some embodiments, the mounts are configured for adjusting respective positions of the first set of one or more lenses and the second set of one or more lenses.

In accordance with some embodiments, a method includes transmitting, to a first lens from a first light element, a first light having a first color (e.g., green light, FIG. 1J); transmitting, to the first lens from a second light element that is distinct and separate from the first light element, a second light having a second color that is distinct from the first color (e.g., blue light, FIG. 1J); directing, with the first lens, the first light from the first light element in a first direction and the second light from the second light element in a second direction that is distinct from the first direction; and directing, with a first set of one or more lenses, the first light and the second light from the first lens toward a first eye of a user.

In some embodiments, the first light is spatially offset from the second light upon reaching the first eye of the user (e.g., in FIG. 1J, the green light is laterally offset from the blue light upon reaching eye 140-1).

In some embodiments, the method also includes transmitting, to the first lens from a third light element that is distinct and separate from the first light element and the second light element, a third light having a third color that is distinct from the first color and the second color (e.g., red light, FIG. 1J); directing, with the first lens, the third light from the third light element in a third direction that is distinct from the first direction and the second direction; and directing, with the first set of one or more lenses, the third light from the first lens toward the first eye of the user.

In some embodiments, the method also includes transmitting a fourth light having the second color to the first lens from a fourth light element that is distinct and separate from the first light element, the second light element, and the third light element; transmitting a fifth light having the third color to the first lens from a fifth light element that is distinct and separate from the first light element, the second light element, the third light element, and the fourth light element; directing, with the first lens, the fourth light from the fourth light element in a fourth direction that is distinct from the first direction, the second direction, and the third direction and directing, with the first lens, the fifth light from the fifth light element in a fifth direction that is distinct from the first direction, the second direction, the third direction, and the fourth direction; and directing, with the first set of one or more lenses, the fourth light and the fifth light from the first lens toward the first eye of the user.

In some embodiments, the method also includes transmitting a fourth light having the second color to the first lens from a fourth light element that is distinct and separate from the first light element and the second light element; directing, with the first lens, the fourth light from the fourth light element in a fourth direction that is distinct from the first direction and the second direction; and directing, with the first set of one or more lenses, the fourth light from the first lens toward the first eye of the user.

In some embodiments, the first light and the second light are separated by at least 2 mm at a location adjacent to an entrance pupil of the first eye.

In some embodiments, the method also includes transmitting, from a reference light element to the first set of one or more lenses, a reference light having the first color without transmitting the reference light through the first lens, a color of the reference light having been selected based on information stored in the device. In some cases, the reference light is transmitted to indicate to the user which color indicates an alignment of the first set of one or more lenses with the first eye. In some embodiments, the reference light element is selected based on information recorded during manufacturing of a device that includes the first lens, the first light element, and the second light element (e.g., the head-mounted display device) (e.g., information indicating a color of light received by a camera that is in alignment with the first lens).

In some embodiments, the first light and the second light are separated by no more than a diameter of an entrance pupil of the first eye at a location adjacent to the entrance pupil of the first eye.

In some embodiments, the method also includes transmitting, to a second lens from a sixth light element, a sixth light having the first color; transmitting, to the second lens from a seventh light element that is distinct and separate from the sixth light element, a seventh light having the second color; directing, with the second lens, the sixth light from the sixth light element in a sixth direction and directing, with the second lens, the seventh light from the seventh light element in a seventh direction that is distinct from the sixth direction; and directing, with a second set of one or more lenses, the sixth light and the seventh light from the second lens toward a second eye of the user that is distinct from the first eye of the user.

In some embodiments, the method also includes adjusting a representative position of the first set of one or more lenses and/or a representative position of the second set of one or more lenses based on a color of light received the first eye of the user and/or a color of light received by the second eye of the user. In some embodiments, adjusting the representative position of the first set of one or more lenses includes moving the first set of one or more lenses laterally. In some embodiments, adjusting the representative position of the second set of one or more lenses includes moving the second set of one or more lenses laterally. In some embodiments, adjusting the representative position of the first set of one or more lenses and/or the representative position of the second set of one or more lenses includes adjusting a representative distance between the first set of one or more lenses and the second set of one or more lenses. In some embodiments, adjusting the representative position of the first set of one or more lenses and/or the representative position of the second set of one or more lenses includes adjusting an interpupilary distance between the first set of one or more lenses and the second set of one or more lenses. In some embodiments, adjusting the representative position of the first set of one or more lenses and/or the representative position of the second set of one or more lenses includes concurrently adjusting the representative position of the first set of one or more lenses and the representative position of the second set of one or more lenses.

In accordance with some embodiments, a method includes receiving, with a first eye of a user, a portion of a first bundle of light that includes a first light and a second light that is distinct from the first light and laterally offset from the first light, the first light and the second light having been transmitted through a first set of one or more lenses; and, in accordance with a determination that the received portion of the bundle of light corresponds to the second light, adjusting a position of the first set of one or more lenses.

In accordance with some embodiments, a method includes receiving, with a camera, a portion of a first bundle of light that includes a first light and a second light that is distinct from the first light and laterally offset from the first light, the first light and the second light having been transmitted through a first lens and a first set of one or more lenses that does not include the first lens, the camera being aligned with the first set of one or more lenses; and storing information associated with a color of the received portion of the first bundle of light in a computer readable storage medium.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings.

For example, in accordance with some embodiments, a device includes a first light source device configured to transmit a first light in a first direction (e.g., and not in a second direction that is distinct from the first direction). In some embodiments, the first light source device includes barrier 146 with an opening (e.g., a pinhole or a slit) and light emitting component 142-2, but not light emitting components 142-1 and 142-3 shown in FIG. 1G. In some embodiments, the first light source device includes lens 144 (e.g., a cylinder lens) and light emitting component 142-2, but not light emitting components 142-1 and 142-3 shown in FIG. 1F. The device also includes a first set of one or more lenses configured for directing the first light toward a first eye of a user. The first light is spatially restricted (e.g., a beam of the first light directed toward the first eye of the user has a width or a diameter less than 5 mm, 4 mm, 3 mm, 2 mm, or 1 mm). The first light provides a cue for adjusting a location of the first set of one or more lenses. In some embodiments, the first light is transmitted through a lateral center of the first set of one or more lenses. Thus, when a user sees the first light with the first eye, this indicates that the first set of one or more lenses is aligned with the first eye. When the user does not see the first light with the first eye, this indicates that the first set of one or more lenses is not aligned with the first eye.

The embodiments described herein were chosen in order to best explain the principles underlying the claims and their practical applications, to thereby enable others skilled in the art to best use the embodiments with various modifications as are suited to the particular uses contemplated.

What is claimed is:

1. A head-mounted display device, comprising:
a first light source device that includes:
   a first light element configured to transmit a first light having a first color;
   a second light element configured to transmit a second light having a second color that is distinct from the first color, the second light element being distinct and separate from the first light element; and
   a first lens configured for directing the first light from the first light element in a first direction and directing the second light from the second light element in a second direction that is distinct from the first direction; and
a first set of one or more lenses configured for directing the first light and the second light from the first lens toward a first eye of a user, wherein:
   the first lens defines a first optical axis, and
   the first set of one or more lenses defines a second optical axis positioned away from the first optical axis.

2. The device of claim 1, further comprising:
one or more electronic displays that include an array of light elements, including a reference light element configured to transmit a reference light having the first color based on information stored in the device, wherein the one or more electronic displays are configured to display one or more images and the first set of one or more lenses are configured to direct light from the one or more electronic displays toward the first eye of the user.

3. The device of claim 1, wherein:
the first light source device also includes:
   a third light element configured to transmit a third light having a third color that is distinct from the first color and the second color, the third light element being distinct and separate from the first light element and the second light element;
the first lens is configured for directing the third light from the third light element in a third direction that is distinct from the first direction and the second direction; and
the first set of one or more lenses are configured for directing the third light from the first lens toward the first eye of the user.

4. The device of claim 3, wherein:
the first light source device also includes:
   a fourth light element configured to transmit a fourth light having the second color, the fourth light element being distinct and separate from the first light element, the second light element, and the third light element; and
   a fifth light element configured to transmit a fifth light having the third color, the fifth light element being distinct and separate from the first light element, the second light element, the third light element, and the fourth light element;
the first lens is configured for directing the fourth light from the fourth light element in a fourth direction that is distinct from the first direction, the second direction, and the third direction and directing the fifth light from the fifth light element in a fifth direction that is distinct from the first direction, the second direction, the third direction, and the fourth direction; and
the first set of one or more lenses are configured for directing the fourth light and the fifth light from the first lens toward the first eye of the user.

5. The device of claim 4, wherein:
the first light element is located on the first optical axis.

6. The device of claim 1, wherein:
the first light source device also includes:
   a fourth light element configured to transmit a fourth light having the second color, the fourth light element being distinct and separate from the first light element and the second light element;
the first lens is configured for directing the fourth light from the fourth light element in a fourth direction that is distinct from the first direction and the second direction; and
the first set of one or more lenses are configured for directing the fourth light from the first lens toward the first eye of the user.

7. The device of claim 1, wherein:
the first light source device, the first lens, and the first set of one or more lenses are configured so that the first light and the second light are separated by at least 2 mm on an entrance pupil of the first eye.

8. The device of claim 1, wherein:
the first light source device, the first lens, and the first set of one or more lenses are configured so that the first light and the second light are separated by no more than a diameter of an entrance pupil of the first eye.

9. The device of claim 1, further comprising:
a second light source device that includes:
   a sixth light element configured to transmit a sixth light having the first color;
   a seventh light element configured to transmit a seventh light having the second color, the seventh light element being distinct and separate from the sixth light element; and
   a second lens configured for directing the sixth light from the sixth light element in a sixth direction and directing the seventh light from the seventh light element in a seventh direction that is distinct from the sixth direction; and
a second set of one or more lenses configured for directing the sixth light and the seventh light from the second lens toward a second eye of the user that is distinct from the first eye of the user.

10. The device of claim 9, further comprising:
mounts configured for holding the first set of one or more lenses and the second set of one or more lenses and adjusting a distance between the first set of one or more lenses and the second set of one or more lenses.

11. A method, comprising:
transmitting, to a first lens from a first light element, a first light having a first color;
transmitting, to the first lens from a second light element that is distinct and separate from the first light element, a second light having a second color that is distinct from the first color;
directing, with the first lens, the first light from the first light element in a first direction and the second light from the second light element in a second direction that is distinct from the first direction; and
directing, with a first set of one or more lenses, the first light and the second from the first lens toward a first eye of a user, wherein:
   the first lens defines a first optical axis, and
   the first set of one or more lenses defines a second optical axis positioned away from the first optical axis.

12. The method of claim 11, further comprising:
transmitting, from a reference light element to the first set of one or more lenses, a reference light having the first color without transmitting the reference light through the first lens, a color of the reference light having been selected based on information stored in the device.

13. The method of claim 11, further comprising:
transmitting, to the first lens from a third light element that is distinct and separate from the first light element and the second light element, a third light having a third color that is distinct from the first color and the second color;
directing, with the first lens, the third light from the third light element in a third direction that is distinct from the first direction and the second direction; and
directing, with the first set of one or more lenses, the third light from the first lens toward the first eye of the user.

14. The method of claim 13, further comprising:
transmitting a fourth light having the second color to the first lens from a fourth light element that is distinct and separate from the first light element, the second light element, and the third light element;
transmitting a fifth light having the third color to the first lens from a fifth light element that is distinct and separate from the first light element, the second light element, the third light element, and the fourth light element;
directing, with the first lens, the fourth light from the fourth light element in a fourth direction that is distinct from the first direction, the second direction, and the third direction and directing, with the first lens, the fifth light from the fifth light element in a fifth direction that is distinct from the first direction, the second direction, the third direction, and the fourth direction; and
directing, with the first set of one or more lenses, the fourth light and the fifth light from the first lens toward the first eye of the user.

15. The method of claim 11, further comprising:
transmitting a fourth light having the second color to the first lens from a fourth light element that is distinct and separate from the first light element and the second light element;
directing, with the first lens, the fourth light from the fourth light element in a fourth direction that is distinct from the first direction and the second direction; and
directing, with the first set of one or more lenses, the fourth light from the first lens toward the first eye of the user.

16. The method of claim 11, wherein:
the first light and the second light are separated by at least 2 mm at a location adjacent to an entrance pupil of the first eye.

17. The method of claim 11, wherein:
the first light and the second light are separated by no more than a diameter of an entrance pupil of the first eye at a location adjacent to the entrance pupil of the first eye.

18. The method of claim 11, further comprising:
transmitting, to a second lens from a sixth light element, a sixth light having the first color;
transmitting, to the second lens from a seventh light element that is distinct and separate from the sixth light element, a seventh light having the second color;
directing, with the second lens, the sixth light from the sixth light element in a sixth direction and directing, with the second lens, the seventh light from the seventh light element in a seventh direction that is distinct from the sixth direction; and
directing, with a second set of one or more lenses, the sixth light and the seventh light from the second lens toward a second eye of the user that is distinct from the first eye of the user.

19. The method of claim 18, further comprising:
adjusting a representative position of the first set of one or more lenses and/or a representative position of the second set of one or more lenses based on a color of light received the first eye of the user and/or a color of light received by the second eye of the user.

20. A method, comprising:
receiving, with a first eye of a user, a portion of a first bundle of light that includes a first light and a second light that is distinct from the first color light and laterally offset from the first light, the first light and the second light having been transmitted through a first lens and a first set of one or more lenses, wherein:
the first lens defines a first optical axis, and
the first set of one or more lenses defines a second optical axis positioned away from the first optical axis; and,
in accordance with a determination that the received portion of the bundle of light corresponds to the second light, adjusting a position of the first set of one or more lenses.

* * * * *